(12) United States Patent
Rustad et al.

(10) Patent No.: US 7,267,120 B2
(45) Date of Patent: Sep. 11, 2007

(54) SMALL VOLUME NEBULIZER

(75) Inventors: Andre Rustad, Etiwanda, CA (US);
David Rivera, Yorba Linda, CA (US);
Charlie Atlas, Coto de Caza, CA (US)

(73) Assignee: Allegiance Corporation, McGaw Park, IL (US)

( * ) Notice: Subject to any disclaimer, the term of this patent is extended or adjusted under 35 U.S.C. 154(b) by 533 days.

(21) Appl. No.: 10/223,394

(22) Filed: Aug. 19, 2002

(65) Prior Publication Data
US 2004/0031485 A1  Feb. 19, 2004

(51) Int. Cl.
*A61M 1/02* (2006.01)
*A61M 15/00* (2006.01)

(52) U.S. Cl. ............... 128/200.18; 128/200.21; 128/203.12; 261/DIG. 65; 239/338

(58) Field of Classification Search .................. 128/200.14–200.24, 203.12, 203.15, 207.14–207.18; 239/338, 343, 370, 369
See application file for complete search history.

(56) References Cited

U.S. PATENT DOCUMENTS

| 190,789 A | 5/1877 | Smyth |
| 2,535,844 A | 12/1950 | Emerson |

(Continued)

FOREIGN PATENT DOCUMENTS

| DE | 1 813 993 | 6/1970 |

(Continued)

OTHER PUBLICATIONS

Professional Medical Products, Inc., Why BetaMist2 is more effective than other nebulizers.

(Continued)

*Primary Examiner*—Glenn K. Dawson
(74) *Attorney, Agent, or Firm*—Michael D. Steffensmeier

(57) ABSTRACT

An atomizing nebulizer for dispensing a substance or medicament is described. The nebulizer is formed with a reservoir base releasably secured to an effluent vent cap that together capture a diffuser and integral dispersing baffle that are further formed with an uptake lumen or channel terminating with a nozzle jet. The diffuser dispersing baffle is positioned relative to the jet nozzle to optimize atomization of any of a number of such substances so as to maximize disbursement of the substance. The reservoir base also incorporates a pressurized fluid-accelerating inlet tube terminated with a metering orifice that cooperates with the nozzle jet when the inlet tube is received within the diffuser uptake lumen or channel. When so received, the nozzle jet axially registers proximate and superior to the orifice to establish a vacuum space that is in fluid communication with a capillary interstice established between the walls of the exterior of the inlet tube and the confronting interior surface of the diffuser lumen or channel. When a pressurized fluid is communicated through the lumen, the orifice, and into the vacuum space towards the nozzle jet, a vacuum develops in the vacuum space that, in combination with the capillary action of the interstice, draws the fluid proximate to the orifice and disperses it into droplets that are then entrained into a fluid stream to be further atomized upon impact with the baffle and then

U.S. PATENT DOCUMENTS

| | | |
|---|---|---|
| 3,114,390 A | 12/1963 | Glättli |
| 3,362,404 A | 1/1968 | Beasley |
| 3,368,555 A | 2/1968 | Beasley |
| 3,371,675 A | 3/1968 | Hatch, Jr. |
| 3,385,295 A | 5/1968 | Beasley |
| 3,389,894 A | 6/1968 | Binder |
| 3,499,459 A | 3/1970 | Swartz |
| 3,507,295 A | 4/1970 | Beeken |
| 3,522,816 A | 8/1970 | Springer |
| 3,537,449 A | 11/1970 | Foxwell et al. |
| 3,586,021 A | 6/1971 | McGuinness |
| 3,598,116 A | 8/1971 | Peters et al. |
| 3,599,653 A | 8/1971 | Clayton |
| 3,630,196 A | 12/1971 | Bird et al. |
| 3,630,217 A | 12/1971 | Bell |
| 3,647,143 A | 3/1972 | Gauthier et al. |
| 3,658,059 A | 4/1972 | Steil |
| 3,659,598 A | 5/1972 | Peters et al. |
| 3,664,337 A | 5/1972 | Lindsey et al. |
| 3,762,409 A | 10/1973 | Lester |
| 3,809,080 A | 5/1974 | Deaton |
| 3,815,593 A | 6/1974 | Baumont |
| 3,817,246 A | 6/1974 | Weigl |
| 3,826,255 A | 7/1974 | Havstad |
| 3,916,889 A | 11/1975 | Russell |
| 4,120,300 A | 10/1978 | Tiep |
| 4,182,486 A | 1/1980 | Mott |
| 4,186,737 A | 2/1980 | Valenta et al. |
| 4,198,969 A | 4/1980 | Virag |
| 4,278,110 A | 7/1981 | Price et al. |
| 4,279,250 A | 7/1981 | Valenta et al. |
| 4,381,002 A | 4/1983 | Mon |
| 4,429,835 A | 2/1984 | Brugger et al. |
| 4,462,398 A | 7/1984 | Durkan et al. |
| 4,509,688 A | 4/1985 | Gagne et al. |
| 4,512,341 A * | 4/1985 | Lester .................. 128/200.21 |
| 4,560,519 A | 12/1985 | Cerny |
| 4,566,452 A * | 1/1986 | Farr ...................... 128/200.21 |
| 4,570,631 A | 2/1986 | Durkan |
| 4,575,042 A | 3/1986 | Grimland et al. |
| 4,657,007 A * | 4/1987 | Carlin et al. ............ 128/200.18 |
| 4,665,911 A | 5/1987 | Williams et al. |
| 4,757,812 A | 7/1988 | Arborelius, Jr. |
| 4,758,224 A | 7/1988 | Siposs |
| 4,832,012 A | 5/1989 | Raabe et al. |
| 4,951,659 A | 8/1990 | Weiler et al. |
| 5,008,048 A | 4/1991 | Ryder |
| 5,054,477 A | 10/1991 | Terada |
| 5,062,419 A | 11/1991 | Rider |
| 5,170,782 A | 12/1992 | Kocinski |
| 5,209,225 A | 5/1993 | Glenn |
| 5,241,954 A | 9/1993 | Glenn |
| H1282 H | 2/1994 | Joyce et al. |
| 5,287,847 A | 2/1994 | Piper et al. |
| 5,309,900 A | 5/1994 | Pari |
| 5,312,046 A | 5/1994 | Knoch et al. |
| 5,318,015 A | 6/1994 | Månsson et al. |
| 5,379,760 A | 1/1995 | Ryder |
| 5,458,136 A | 10/1995 | Pari |
| 5,461,695 A | 10/1995 | Knoch |
| 5,479,920 A | 1/1996 | Piper et al. |
| 5,503,139 A * | 4/1996 | McMahon et al. ..... 128/200.18 |
| 5,505,193 A | 4/1996 | Ballini et al. |
| 5,522,497 A | 6/1996 | Ryder |
| 5,533,497 A | 7/1996 | Ryder .................. 128/200.21 |
| 5,533,501 A | 7/1996 | Denyer |
| 5,549,102 A | 8/1996 | Pari |
| 5,570,682 A | 11/1996 | Johnson |
| 5,584,285 A | 12/1996 | Salter et al. |
| 5,630,409 A * | 5/1997 | Bono et al. ............ 128/200.18 |
| 5,666,945 A | 9/1997 | Davenport |
| 5,687,912 A | 11/1997 | Denyer |
| 5,738,086 A | 4/1998 | McMahon et al. ..... 128/200.21 |
| 5,740,966 A | 4/1998 | Pari |
| 5,771,882 A | 6/1998 | Psaros et al. |
| 5,782,232 A | 7/1998 | Rowland |
| 5,823,179 A | 10/1998 | Grychowski et al. |
| 5,875,774 A | 3/1999 | Clementi et al. |
| 5,957,389 A | 9/1999 | Wunderlich et al. |
| 6,044,841 A | 4/2000 | Verdun et al. |
| 6,076,519 A | 6/2000 | Johnson |
| 6,085,741 A | 7/2000 | Becker |
| 6,116,233 A | 9/2000 | Denyer |
| 6,129,080 A | 10/2000 | Pitcher et al. |
| 6,131,568 A | 10/2000 | Denyer et al. |
| 6,176,237 B1 | 1/2001 | Pari |
| 6,237,589 B1 | 5/2001 | Denyer et al. |
| 6,338,443 B1 | 1/2002 | Piper |
| 6,363,932 B1 | 4/2002 | Forchione et al. |
| 6,450,163 B1 | 9/2002 | Blacker et al. |
| 6,513,519 B2 | 2/2003 | Gallem |
| 6,513,727 B1 | 2/2003 | Pari |
| 6,557,549 B2 | 5/2003 | Schmidt et al. |
| 6,595,203 B1 | 7/2003 | Bird |
| 6,606,990 B2 | 8/2003 | Stapleton et al. |
| 6,612,303 B1 | 9/2003 | Grychowski et al. |
| 6,644,304 B2 | 11/2003 | Grychowski et al. |
| 6,748,945 B2 | 6/2004 | Grychowski et al. |
| 6,772,754 B1 | 8/2004 | Mendenhall |
| 6,848,443 B2 | 2/2005 | Schmidt et al. |
| 6,929,003 B2 * | 8/2005 | Blacker et al. ........ 128/203.12 |
| 6,994,083 B2 | 2/2006 | Foley et al. |
| 2002/0029779 A1 | 3/2002 | Schmidt et al. |
| 2002/0121275 A1 | 9/2002 | Johnson et al. |
| 2002/0157663 A1 | 10/2002 | Blacker et al. |
| 2003/0000527 A1 | 1/2003 | Stenzler et al. |
| 2003/0005929 A1 | 1/2003 | Grychowski et al. |
| 2003/0015193 A1 | 1/2003 | Grychowski et al. |
| 2003/0136399 A1 | 7/2003 | Foley et al. |
| 2003/0226562 A1 | 12/2003 | Schmidt et al. |
| 2004/0173209 A1 | 9/2004 | Grychowski et al. |
| 2004/0231665 A1 | 11/2004 | Lieberman et al. |
| 2005/0081844 A1 | 4/2005 | Grychowski et al. |
| 2005/0121023 A1 | 6/2005 | Braithwaite |
| 2005/0145243 A1 | 7/2005 | Trombi |
| 2005/0166918 A1 | 8/2005 | Trombi |
| 2005/0205085 A1 | 9/2005 | Blacker et al. |
| 2005/0229929 A1 | 10/2005 | Ivri |

FOREIGN PATENT DOCUMENTS

| | | |
|---|---|---|
| DE | 80 30 714 | 3/1981 |
| DE | 30 43 377 | 7/1982 |
| DE | 83 02 105 | 5/1983 |
| DE | 87 03 534 | 10/1987 |
| DE | 87 13 260 | 11/1987 |
| DE | 42 25 928 | 2/1994 |
| DE | 295 09 286 | 10/1995 |
| DE | 195 20 622 | 12/1996 |
| DE | 694 15 639 | 5/1999 |
| DE | 199 02 844 | 11/1999 |
| DE | 199 02 845 | 11/1999 |
| DE | 199 02 847 | 5/2000 |
| DE | 695 14 986 | 6/2000 |
| DE | 199 62 110 | 6/2003 |
| EP | 0 052 284 | 5/1982 |
| EP | 0 170 715 | 2/1986 |
| EP | 0 281 650 | 9/1988 |
| EP | 0 540 774 | 5/1993 |
| EP | 0 582 124 | 2/1994 |
| EP | 0 652 021 | 5/1995 |
| EP | 0 711 609 | 5/1996 |
| EP | 0 747 076 | 12/1996 |
| EP | 0 626 180 | 8/1999 |

| | | |
|---|---|---|
| GB | 2 358 356 | 7/2001 |
| WO | WO86/01731 | 3/1986 |
| WO | WO94/05357 | 3/1994 |
| WO | WO97/22376 | 6/1997 |
| WO | WO97/29799 | 8/1997 |
| WO | WO 00/27455 | 5/2000 |
| WO | WO 02/40085 | 5/2002 |
| WO | WO 02/073470 | 9/2002 |

OTHER PUBLICATIONS

Professional Medical Products, Inc., Beta Gard System, product literature, BMIST 2 nebulizer.

* cited by examiner

FIG. 10
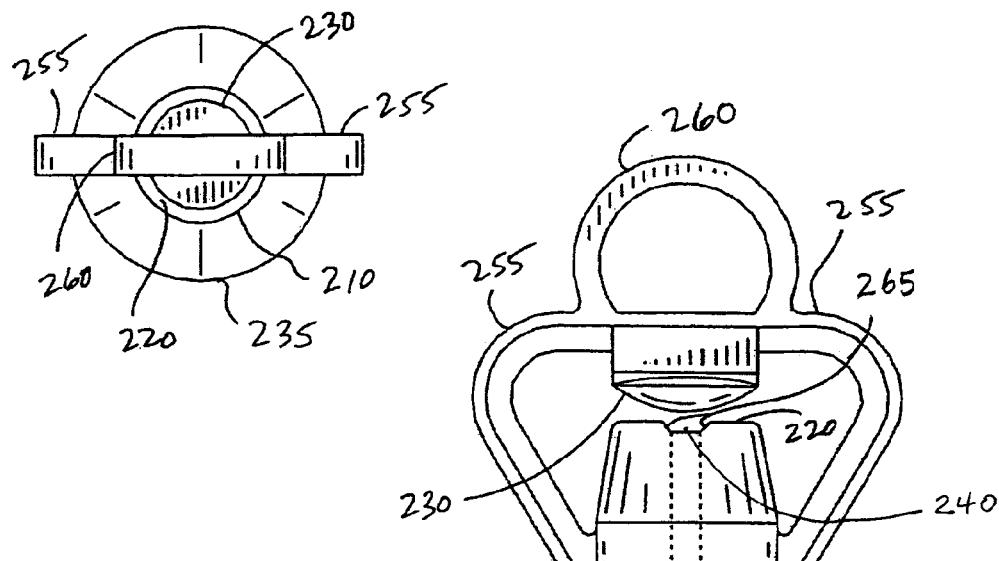
FIG. 11
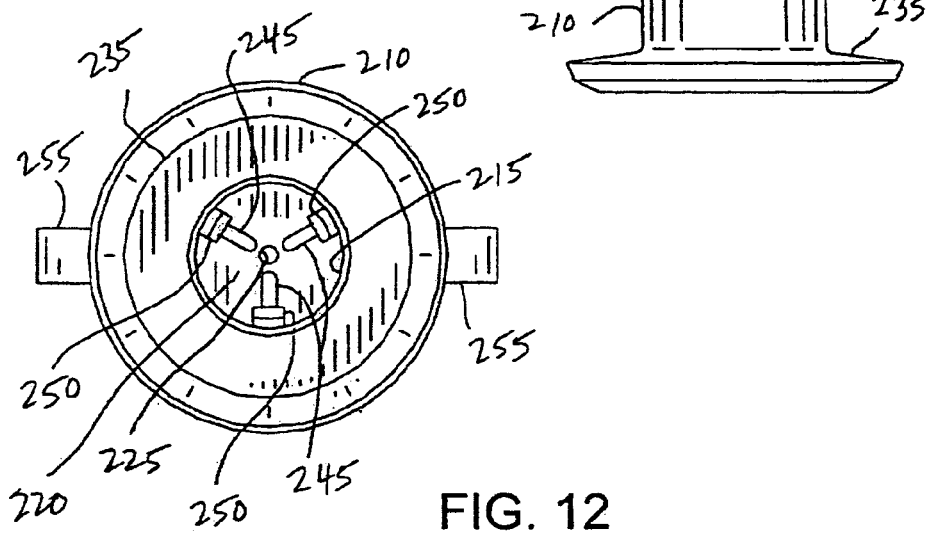
FIG. 12

SMALL VOLUME NEBULIZER

TECHNICAL FIELD

This invention relates to the field of inhalation-based drug and therapeutics delivery systems. Specifically, the present invention is an aerosol generator that is also known to those skilled in the art as a small volume nebulizer, which in various embodiments is adapted to deliver small, suspended and entrained particles of a liquid medication to be inhaled via an ambient air stream, a gaseously controlled air stream, such as pure oxygen, or via a combination of such air-streams.

BACKGROUND OF THE INVENTION

Modern medicine supplies humanity with an unprecedented number and diversity of drugs, medicines, therapeutics, medicaments, treatments, and the like. A physician or health care provider may choose a drug or a combination of drugs and a most preferred means of delivery to the patient based upon several factors. The nature of the condition or disease and the overall state of health of the patient are two such exemplary factors. Additional examples include the type of medicine to be delivered, the therapeutic objective(s) to be achieved, the costs of the medicine and the available delivery options, and the time period in which the medicament must be administered to the target patient.

While selecting an appropriate course of treatment can be a challenging task, it is often only half of the battle. The physician must also choose a delivery method and system most suited to the particular ailment(s), the patient (whether it be an infant or incapacitated adult), the medicament to be delivered, and the time within which the medicine(s) must be received by the patient. Although each of these considerations are important in themselves, as those skilled in the art can appreciate, one of the most salient decisions facing the health care provider is the route of delivery.

The physician typically considers many variables before selecting a drug delivery route. Such factors include, for example, the target location in the body, the ease of administration, and the stability, solubility, miscibility, aerosolability, dispersability, and toxicity of the medicament and therapeutic agents. While considering these and other factors, the physician selects from delivery routes including needle injection to the veins, muscles, tissues, or cavities of the body; needle-free injection systems using pressurized gas; direct application to the dermis; direct application to a mucous membrane; inhalation or inspiration; and ingestion. Although these and other routes of drug delivery are possible, one of the more common routes of drug delivery for various physical anomalies is inhalation of aerosolized medicaments, which is used specifically for pulmonary and other types of respiratory ailments as well as where immediate non-vascular infusion of assimilable medicaments into the bloodstream is needed.

Inhalation-based drug delivery offers several advantages over other possible routes. One such advantage is that, since conscious patients can be very comfortable with inhaled medicaments, they can often medicate themselves easily and reliably by inspiring their desired medicines. Inhalation of therapeutics is therefore widely applicable to diverse patient populations. This issue is particularly important for long-term treatments and in treating infants and other patients with limited mobility, loss of fine motor control, or other incapacitation. A second advantage of inhaled medicine is the rapidity of drug dispersion throughout the body. If properly delivered to the highly vascularized pulmonary system of the lungs, and depending upon the medicament(s) to be administered, inhaled medicine can quickly enter the circulatory system via the pulmonary tract without the discomfort, invasiveness, risks of infection, or requisite skill associated with needle-based administration.

Furthermore, patients with collapsed, obscured, or otherwise difficult circulatory vessels can often benefit from inspiring their medicine. Not only can inhalation be easier for the patient, it can actually help to preserve the integrity of the therapeutic agent and prevent harm to possible distressed circulatory vessels. Further, an inhaled drug is not exposed to the harsh, acidic environment of the gastrointestinal tract. The conditions in the stomach can degrade, alter, or otherwise compromise many medicines, resulting in a potentially serious loss of efficacy. These same medicines may be stably delivered by inhalation, thereby preserving the anticipated function. Additionally, the potential discomfort to the patient and possible harm to the gastrointestinal tract resulting from use of medicaments known to have adverse effects thereupon can otherwise become a source of discomfort to the patient for myriad other reasons, can be sometimes avoided by inhalation treatment methods.

Yet another advantage of inhaled medicament therapeutics is the temporal flexibility of this method compared to ingestion. For example, physicians often warn patients to ingest their prescribed or preferred medicines either concurrently in time with mealtimes, and or with a specific food or a specific beverage, or without certain foods or beverages, or within a desired period of time proximate to such mealtimes or consumption of such specific foods or beverages. These admonitions and sometime requirements may force a patient to adjust their diet or other routines in order to accommodate their medication schedule, and this type of adjustment is often difficult if not impossible for the patient with child care and employment duties and other demands. Far more dangerous is the possibility that the patient will inappropriately take their medicine with or without such specific foods or beverages, or with the wrong type of food, or at the wrong time. Any of these scenarios might result in possible discomfort at best, and at worst potentially serious side effects, synergistic reactions, or a loss of drug efficacy. Depending upon the ailment being treated, the condition of the patient, and the proposed medicament(s), many of these considerations may not apply to inhaled medicines and corresponding treatment regimens.

In light of these and other advantages, it is unsurprising that inhalation is often the only, the best, or the preferred method of drug delivery. This can be especially true for pulmonary and respiratory related ailments wherein the medicament must be administered directly to the affected tissues immediately upon expression of particular symptoms. For example, asthmatic patients can experience distressing and sometimes fatal consequences resulting from asthmatic episodes that can have unknown origins or that can be triggered from foods, beverages, physical activity, exposure to various airborne substances or particles, or from exposure to stressful events. Such asthmatic individuals can significantly benefit from timely administered inhaled medicaments that can attenuate if not even completely avoid the more severe symptoms of asthma. One such effective medicament that is widely used in treating asthma and other ailments, and which is delivered via inhalation using any of a number of suitable devices is albuterol, which in 1994 was found to be the $14^{th}$ most prescribed medicine of any kind by the National Center for Health Statistics, U.S. Dept. of Health and Human Services. Such proposed inhalation treatment regimens can often be very effective is ameliorating the symptoms quickly and without unduly undesirable side effects or other adverse consequences. And, such results can be accomplished with what are generally accepted to be relatively small doses of such medicaments. Those skilled in the art often refer to such small dosages as being in the range of approximately between 0.5 and 30 cubic centimeters or "CCs" (also referred to as milliliters wherein 1 milliliter is equal to 1 CC), and more preferably in the range of about 1 to 20 CCs, and even more preferably in the range of about 5 to 10 CCs. Other exemplary treatment substances and medicaments include inhalable antibiotics that can be useful in treating pseudomonas and related lung infections in Cystic Fibrosis patients.

Once a physician decides to administer this or another medicine via inspiration, several considerations remain. A first and fundamental consideration is to obtain the medicine in an inhalable form. Relatively few drugs are gaseous, and the process of sublimating or otherwise phase transitioning a liquid or solid drug to a gas can be costly, inefficient, can compromise or ruin the drug, or can be otherwise difficult or impossible. To overcome these difficulties, the most common approach to inhalation-based delivery is to disperse and suspend tiny droplets of a gas or a vapor or a liquid, or solid particles, of medicament in an airstream of ambient atmospheric air, some other gas such as oxygen or an artificial atmosphere, or some combination thereof, and then to deliver the dispersed suspension to the patient. Those with skill in the art may know this process as atomizing, aerosolizing, or nebulizing. A device that is used that incorporates this process is customarily known to those knowledgeable in the arts as an atomizer, a nebulizer, an aerosol dispenser, and more colloquially sometimes as an inhaler or a vaporizer.

Those skilled in the art employ many variations of nebulizers or atomizers and usually divide the various dispensing devices into 2 or more categories, which can be used in a variety of medical and industrial applications. For purposes of administering the small dosages known to be effective in treatment of various ailments to inhalation regimen treatments, those skilled in the art often refer to such nebulizers and atomizers as "small volume nebulizers," among other commonly used phrases and names. In medical applications, further subcategories exist that classify such devices as to their intended disposable or reusable applications including, for example, devices that are compatible for use with the patient's own natural breathing rhythms, pressurized air ventilators such as those used in critical care environments, and intermittent positive pressure breathing equipment. A first type of device is a 2-phase system wherein the constituent medicine or substance to be dispensed in the nebulized or aerosolized air stream is mixed with either (1) a pressurized liquid propellant stream that expands into a gas upon release, (2) a pressurized gaseous propellant that expands into lower-pressure gas stream upon release, or some combination thereof. In this type of 2-phase system, various mechanical devices can be used in conjunction with the dispenser to further break up the now dispersed and suspended droplets or particles into even smaller droplets or particles. Other types of such dispensing devices include 3-phased and other multi-phased aerosol dispensers that can employ similar approaches wherein, for further example, the device incorporates a non-mixing liquified propellant with the proposed gaseous propellant, which are both dispensed with the constituent medicament or substance so as to further increase the dispersal of the constituent component in suspension in the dispensed nebulized or aerosolized air stream.

In the more common, present day drug delivery nebulizer devices and applications, those with skill in the art have made attempts to fabricate nebulizers and atomizers to have several functional components that can include, for purposes of illustrating various prior art devices, a base or reservoir for holding a substance or medicament to be dispensed, an air nozzle jet and capillary uptake feature that is adapted to disperse the substance into an airstream impinging upon a diffuser or baffle. The diffuser or baffle is usually designed for one or more capabilities. One capability is to break apart into smaller pieces the droplets or particles suspended in the incident airstream; another desirable function is to block large particles while passing particles or droplets that have been dispersed and atomized or nebulized into smaller particles or droplets having a maximum average diameter or size.

Such prior art attempts have been often touted to ideally atomize the dispersed substance into particles or droplets to have an average maximum diametrical dimension that is adapted either to be inhaled into the bronchial or to be inhaled into the even smaller alveoli airways in the lungs of the patient, or both. Atomization to obtain such desirable particle or droplet sizes has long been sought in the industry as has been noted in, for example, U.S. Pat. No. 3,762,409 to Lester, which recognized that droplets that are too small may be exhaled without effect and that droplets that are too large may be retained in the upper respiratory tracts without reaching the lower regions needing treatment) and U.S. Pat. No. 6,338,443 B1 to Piper, which noted that the most respirable droplet sizes are between 2 to 4 micrometers.

There have been many attempts at producing a variety of nebulizer and atomizer devices, all of which have demonstrated significant shortcomings and inefficiencies. Most notably among the problems in the prior art, it has been found that such devices usually produce unpredictable and widely varying results in terms of the efficiency of the dispensed aerosol substance. Such variations and uncertainty is pervasive in the industry without regard to manufacturer, device, or to the proposed approach, as may be illustrated in detailed descriptions of various U.S. patents, some of which are briefly described herein. Such unpredictability and variance has continued to plague the art and has thereby established a present and immediate need for improvement so that medical practitioners can achieve consistent and predictable results in prescribing aerosol-based treatment regimens that will have the anticipated and desired results.

One of the specific issues that persists in the prior art devices and that has received considerable attention in the prior art includes the difficulty in achieving desired particle or droplet sizes by fabricating such devices to have precise configurations and arrangements of elements between certain components so as to establish predictable atomization and nebulization of the substances to be dispensed in aerosol or atomized form. Another prevalent problem includes the inability of many of the prior art devices to utilize all of the substance to be dispensed that is received in the dispensing device. One additional especially notable problem in the art is that most of such devices must be used in a specific horizontal or vertical orientation, which depends upon the particular construction of the device. If not so used, the device will not operate as advertised to disperse, aerosolize, and dispense the treatment substance as expected, if at all.

One such prior art attempt is described in the U.S. Pat. No. 6,338,443 to Piper, which is limited to a high efficiency medical nebulizer that incorporates, among other elements, a housing that receives an intermediate section formed with various flow regulating orifices adapted to establish a jet spray, a lower liquid supply jar, an upper inhaler cap, an aerosol amplifier surface, and spray posts adapted to capture and prevent the release of droplets that are larger than desirable for the aerosol effluent. One of the various problems with the proposed '443 device that may be apparent to those knowledgeable in the relevant arts includes the unpredictability of the content of the substance to be dispensed in the effluent aerosol that is the result of the unpredictable distance that will be established between the amplifier surface and the orifices that create the spray.

Although many sources of unpredictability exist with the '443 Piper device, one of the more obvious sources of mostly uncontrollable variance exists in the fact that the manufacturing tolerances inherent in fabricating the inhaler cap and the integral amplifier surface, as well as the intermediate section, and the jar will result in an assembled device that multiplies the variance that exists in each of the components such that the distance between the amplifier surface and the jet spray orifices can be unacceptably misaligned or large or small. Since the distance between the amplifier surface and the orifices of the intermediate section cannot be reliably controlled during fabrication to an acceptable degree, at least without unusual and extraordinary manufacturing techniques, the resulting aerosol will necessarily contain an unpredictable amount of the substance that is to be dispensed in the effluent airstream. Additionally, in operation, it is likely that an untrained or inattentive user could easily improperly assemble the '443 device inducing even further misalignment and or establishing an undesired distance between the amplifier surface and the orifice, which would be compounded upon that already described above.

In further prior art attempts at addressing some of the problems of the prior art, U.S. Pat. Nos. 5,503,139 and 5,738,086, both to McMahon et al. teach, among other elements, the use of multiple individual components for the diffuser orifices and target baffles, which individual components are assembled after manufacture much in the same way as the Piper '443 device. These same problems were also evident in earlier proposed devices, including those described by Lester in U.S. Pat. No. 3,762,409 and suggested by Svoboda in U.S. Reissue Pat. No. RE 33,717. Other prior attempts amplify the inherent possible errors in establishing a critical distance between the jet creating diffuser orifice and the target baffle. In U.S. Pat. No. 5,533,497 to Ryder, among other features and design constraints, multiple components are required to be threadably assembled to establish the desired critical distance, which critical distance is specifically reliant upon complete threaded receipt of a housing component to a cap, which as already described, can have unexpected results in the hands of an unaware or untrained operator. In U.S. Pat. No. 4,657,007 to Carlin et al., another approach is suggested wherein certain components may be integrally formed via injection molding so as to improve manufacturability, among other purported advantages. However, even the Carlin et al. '007 device suffers from the same critical distance uncertainty problems rife in the present day technology in that the '007 device is limited to nebulizer having a separate friction fit-type cap and target component that must be properly seated on a conduit formed with the spray creating orifice so as to establish the desired atomization of the treatment substance. Here again, the Carlin et al. reference fails to appreciate the likelihood that the uncaring or unknowledgeable user will improperly seat the cap and target member so as to create the uncertain performance characteristics so common in the devices presently available on the market and known to those skilled in the art.

In addition to the difficulty or inability to precisely control the distances of import as noted above, many of these devices are also limited to embodiments having unnecessarily complicated effluent airstream pathways and that are restricted to difficult to manufacture constructions that often require expensive thermoplastic injection molds, all of which result in undesirable manufacturing challenges and increased production costs, as well as the inherent unpredictable performance characteristics.

The inconsistency and unpredictability of the noted approaches can be extremely wasteful, as many nebulizers are undoubtedly manufactured that do not produce particles of the desired size and that must therefore be rejected during post-manufacture inspection, if such is done. Additionally, since many of the prior art devices can have unpredictable performance during use, patients can be subject to under and over-medication, and the prescribed medication can be unavoidably wasted if underutilized by a dispenser device that is not properly aerosolizing and dispensing medicament or where such medicines are overused with the expectation that not enough medicament will be dispensed to the patient in light of the known problems with the prior art devices. The latter issues can be significantly costly for widely used medications that can often cost as much as $100 (See, for example, U.S. Pat. No. 5,738,086) or more per cubic centimeter (also referred to by those skilled in the arts as a "CC" or a milliliter, "mL"). Also, such problems can also result in difficulties for the patient who may use such a nebulizer thinking that medicine is being effectively delivered when in fact such delivery may be uncertain at best and completely absent at worst. The adverse consequences of such difficulty can be even more pronounced for infant or incapacitated patients unable to monitor the uptake of medicine into the effluent airstream of the nebulizer.

What has long been needed in the art is a small volume nebulizer that is easy and relatively inexpensive to manufacture, that both reduces the variability of particle size and is efficient, and that is still compatible with conventional methods of inspiration-based treatment. The present invention overcomes many of the problems prevalent in the prior art in a number of ways and with a wide range of contemplated embodiments, configurations, and alternative and preferred arrangements.

SUMMARY OF INVENTION

In its most general configuration, the present invention advances the state of the art of nebulizers and atomizers, including small volume nebulizers, with a variety of new capabilities, embodiments, and components and overcomes many of the shortcomings of prior devices in new and novel ways. In one of the many preferable configurations, the present invention contemplates a significantly improved nebulizer that is adapted and optimized for dispensing a predetermined fixed quantity or predetermined fixed rate of flow of a preselected treatment substance or medicament that is to be prescribed for and inhaled by a patient who is to undergo pulmonary inhalation treatment.

In one embodiment of a preferred nebulizer according to the principles of the present invention there is included a reservoir base that is sized to receive a treatment substance and that is adapted with a pressurized fluid inlet tube having a decreasing internal taper in the direction of flow, so as to accelerate fluid being communicated through the inlet tube, and terminating at a distal metering orifice that is adapted to regulate the flow of a fluid therethrough. In practice it has been found to be preferable to also minimize the thickness of the wall that defines the entrance and exit of the metering orifice so as to minimize the deceleration and energy loss of a fluid as it passes through and across the edges of the wall that defines the periphery of the metering orifice. Such deceleration and energy can be the result of many interfering attributes including for example, side wall drag or frictional and shearing forces, back pressure induced in the fluid stream at the entrance and exit planes of the metering orifice, separation of boundary layer flow streams at the walls and edges of the fluid passageways due to surface roughness and internal turbulence and fluid stream shear forces, to name a few such sources.

An effluent vent cap is also included that is formed with an aerosol outlet and that is preferably adapted to be removably coupled to the reservoir base to form an interior cistern with an upper recess and a lower substance storage vessel. The effluent vent cap and the reservoir base are preferably adapted with threads, twist-lock elements, or any other of a variety of coupling mechanisms and components known to those skilled in the art and that would be equally effective to releasably join the cap and the base.

When so coupled together, the reservoir base and the effluent vent cap positively capture an interchangeable diffuser. The preferred interchangeable diffuser can be one of a plurality wherein each diffuser is adapted and optimized for a particular treatment regimen, a particular one of a plurality of possible preselected treatment substances. The diffuser preferably includes an uptake lumen or channel that is adapted to be received upon the inlet tube of the reservoir base. The uptake lumen or channel is also adapted, during operation, to be in fluid communication with the preselected substance that may be received in the cistern. The lumen or channel preferably terminates in a nozzle jet configured to spray a jet of fluid against an integrally formed dispersing baffle or baffle disperser that is superiorly positioned proximate to the nozzle jet. The integral formation of the disperser as part of the diffuser as one piece enables the gap and axial alignment between the nozzle jet and the disperser to be the same whether or not a user tightens the effluent vent cap properly to the reservoir base. Conventional nebulizers have the baffle and diffuser orifice contained in separate components, each having dimensional variations inherent in the manufacturing process that make the gap and axial alignment inconsistent. When received and seated on the inlet tube, the nozzle jet is axially aligned superiority proximate to the distal metering orifice.

The precise position, size, shape, and orientation of the dispersing baffle is selected and arranged for purposes of dispersing the sprayed jet of fluid to establish the desired mean average diameter of the resultant droplets or particles, which is a further function of the particular preselected substance or medicament and the prescribed treatment regimen. In any of a number of possible variations, alternatives, and modifications of the embodiments disclosed herein and contemplated for use with the present invention, the jet nozzle or nozzle jet may also further incorporate a diverging spray guide, channel, or groove that is configured to optimize the divergence pattern of fluid being sprayed from the nozzle jet to maximize and optimize atomization into droplets or particles of the preselected substance being sprayed against the dispersing baffle.

The optional diverging spray guide, channel, or groove can be implemented wherein the jet nozzle is formed in a bulkhead of the uptake lumen or channel such that the bulkhead is further formed with a substantially lateral channel defined by at least two generally confronting and parallel or askew sidewalls. The lateral channel is preferably substantially registered and optionally centered about the jet nozzle to minimize the thickness of the bulkhead proximate to the nozzle and whereby the sidewalls are configured to control the divergence of a fluid stream being communicated from the jet nozzle. Various efficiencies can be achieved in regard to minimizing energy loss of flowing or sprayed fluid streams by incorporating such diverging spray guides, channels, or grooves that have sidewalls that are angled relative to each other and about the exit plane of the nozzle jet contemplated herein. While the relative angle has been found to be variably dependent upon the type of fluid, temperature, viscosity, and pressure differentials across the various elements, among other parameters, the relative angle found to be suitable for purposes of optimizing the nebulizer of the present inventions preferably in the range of between about 5 and 47 degrees for compatibility with many of the more commonly contemplated preselected treatment substances and medicaments. Such relative angles are expected to change depending upon the various possible constructions of the present invention and the many possible treatment regimens and preselected treatment substances described and contemplated herein.

Additionally, in variations of any of the contemplated embodiments, the diffuser and the reservoir base are further optionally or preferably adapted to positively and releasably engage one another so as to precisely and positively position and register the nozzle jet of the diffuser uptake lumen or channel proximate to and in registration with the distal metering orifice of the inlet tube, when the lumen or channel is received upon the tube, to establish a predictable and easily repeatable arrangement and registration of the nozzle jet with the distal orifice in a way that establishes positive tactile feedback to the user who is seating the diffuser into the base during setup and configuration. Although many possible configurations exist that are compatible for purposes of practicing the present invention, one suitable configuration includes a nozzle jet that preferably can have a cross-sectional area that is approximately larger than that of the distal metering orifice, which in operation and in combination with the other features and components described herein, creates a suitably capable jet spray impinging upon the dispersing baffle that effectively disperses and atomizes the preselected treatment substance.

The integrally formed uptake lumen, jet nozzle, and dispersing baffle of the diffuser are preferably fabricated whereby the dispersing baffle is precisely aligned with and set at a predetermined distance from and orientation relative to the jet nozzle so as to optimally produce suitably sized droplets or particles in sufficient quantities given a particular preselected substance or medicament so as to effect the desired treatment regimen. In modifications to any of the described embodiments, the predetermined distance and orientation of the dispersing baffle and nozzle jet can be adjusted for optimized droplet and particle nebulization or aerosolization for a particular treatment regimen and preselected substance or medicament. The present invention contemplates such adjustments to the size, shape, position, and arrangement of the dispersing baffle relative to the nozzle jet so as to establish a desirable droplet or particle quantity and size profile that is suited for the particular treatment and for purpose of compatibility with a variety of possible preselected substances, which substances can have variable surface tensions, viscosities, concentrations, and the like.

The preferred diffuser of the present embodiments is also further adapted to cooperate with the reservoir base such that, when the uptake lumen or channel is received about the inlet tube, a capillary interstice is formed between an exterior surface of the inlet tube and the confronting interior surface of the uptake lumen or channel. Additionally, when so arranged, the proximately registered nozzle jet and the distal orifice are preferably operative to define a vacuum space that is in fluid communication with the distal orifice and the capillary interstice and in which a vacuum is developed relative to ambient atmospheric pressure outside the nebulizer, which vacuum is established when a pressurized fluid is communicated via the inlet tube and sprayed through the metering distal orifice towards and through the aligned nozzle jet. In this way, the preselected treatment substance or medicament is drawn into the interstice, under the force of either capillary action or the vacuum pressure differential or both, and into the vacuum space where it is dispersed in droplets or particles of about 10 to 500 μm by the sprayed fluid stream, which can be an air or fluid stream.

The dispersed droplets or particles are thus entrained in the fluid stream and sprayed through the nozzle jet to impinge upon the dispersing baffle, which imparts even more kinetic energy to the droplets or particles sufficient to overcome their internal cohesive and surface tension forces and to break them apart into droplets and particles preferably having even smaller mean average diameters such that the kinetic energy of the entraining fluid stream carries the smaller droplets or particles away from dispersing baffle and out of the nebulizer through the aerosol outlet in the effluent fluid or air stream. While many of such droplets and particles will be small enough to be carried away, the larger of them will be too big and will fall back into the bottom of the cistern to be redrawn into the interstice and re-dispersed.

In another possible optional alternative arrangement of the various embodiments, modifications, and variations of the present invention described herein, those skilled in the art can further understand that the contemplated capillary action of the illustrated interstice can be further enhanced and or amplified by treating one or more of the surfaces of the diffuser and the inlet tube to optimize the surface energy thereof, which in turn can improve the adhesion forces between such surfaces and the substance to be dispensed whereby such treatment can be effected to not only amplify the capillary action of the interstice, but can also establish such adhesion forces to be greater than the internal cohesion forces in the substance to be dispensed. A wide variety of such surfaces is further discussed elsewhere herein and can include, for example, plasma and ionization treatments.

A wide variety of possible shapes, sizes, and configurations of the reservoir base are contemplated for use with the present invention. Although those skilled in the relevant arts can comprehend that many possible and equally effective configurations are possible and within the scope of the contemplated embodiments of the present invention, only one of many such possible configurations is illustrated herein for purposes of illustrating optional or preferable configurations of the reservoir base wherein it is formed to have a generally diminishing lateral cross section from an upper or a superior portion to a lower or an inferior portion whereby the preselected treatment substance that is received in the vessel is thereby forced to pool in the bottom of or about the inferior portion of the reservoir base. This configuration can maximize immersion of a lower part of the diffuser in the pooled substance so that the capillary action and vacuum drawing capabilities of the operating nebulizer can be maximized. Even more specifically, the illustrated embodiments depict the reservoir base to have a substantially lofted ellipsoid surface similar to a chicken egg shape or the shape an ovoid object. Other contemplated shapes can include, for purposes of example, conical, trapezoidal, pyramidal, polygonal, to name just a few. Moreover, although not reflected in the various figures, those skilled in the art should also further appreciate that the present embodiments and alternative configurations of the illustrated reservoir base also contemplate incorporating a supply port for continuous supply of the preselected substance that is to be nebulized and delivered at a predetermined rate of flow such that the reservoir need not be regularly removed and replaced for purposes of refilling after nebulization and depletion of the preselected substance.

Additional embodiments of nebulizers that are contemplated by the apparatus of the present invention can be further modified wherein the aerosol outlet of the effluent vent cap is further formed with a baffle lumen that can be adapted to project interiorly into the upper recess proximate to the vent cap to increase the length of the path a particle may travel in the effluent fluid or air stream after deflecting off of the dispersing baffle or baffle disperser and before exiting through the aerosol outlet. A further variation of any of the preceding embodiments may also incorporate at least one volumetric unit of measure indicia that can preferably be imprinted upon or otherwise formed on or about the reservoir base. The indicia are preferably calibrated to establish the predetermined quantity of the preselected substance to be dispensed once the substance has been received in the lower vessel of the cistern formed when the reservoir base is coupled to the vent cap.

Any of the illustrated embodiments and modifications thereto may also further optionally incorporate at least one support member that can preferably be integrally formed as part of or that can be otherwise attached to the reservoir base to establish free-standing capability of the nebulizer on a substantially level surface during filling with the preselected substance. In various configurations the support member may be formed as a flat inferior surface of the base reservoir much like the bottom surface of a coffee cup or water glass. In other alternative arrangements, the reservoir base may be formed to have any of the variety of lofted surface profiles that may be well-suited to establish a preferred pooling of the preselected treatment substance in the lower vessel of the cistern, but which surface profiles are not well-adapted to rest in an upright position on a level surface without added support members. In this alternative arrangement, the contemplated at least one support member can be one or more legs that are included as part of or integrally formed with the reservoir base to establish the free standing capability.

Any of the preceding alternatives, configurations, and embodiments of the nebulizers practiced in accordance with the principles of the present invention may also be adapted to include any one of a number of components that are adapted to prevent siphoning of the preselected treatment substance out of the cistern when the proposed nebulizer is handled, used, or operated at less than desirable orientations. One such optional anti-siphoning arrangement of the preferred nebulizer incorporates a base reservoir adapted with the pressurized fluid inlet tube to project up and into the cistern sufficiently far so that the superior end of the inlet tube, which incorporates the nozzle jet or the jet nozzle and the optional diverging spray guide or groove, terminates at a distance above the top surface of the preselected substance when received in the cistern of the reservoir base. In this way, under nominal operating orientations, the likelihood is minimized that the preselected treatment substance will leak into the inlet tube and be thereby siphoned out of the cistern. For unusual attitudes and orientations, the effluent vent cap may be similarly configured and further modified to incorporate an analogous anti-siphon feature wherein the aerosol outlet of the effluent vent cap is extended whereby the contemplated baffle lumen is extended even farther into the upper recess, which can prevent leakage of the preselected treatment substance when the nebulizer is at an otherwise unusual orientation.

The present invention also contemplates yet additional variations and alternative arrangements of any of the illustrated embodiments wherein various additional optional means of capturing the diffuser within the cistern are possible. In one such configuration, the reservoir base is formed, about an interior surface that establishes the bottom surfaces of the lower vessel of the cistern, with one or more standoffs that can be shaped, sized, and positioned to optimize the capillary interstice that is formed between the diffuser when it is seated and received upon the inlet tube of the reservoir base. Even further, in optional or preferred embodiments wherein it is desirable to releasably secure the diffuser to the reservoir base in a way that communicates positive tactile feedback to the operator during setup and operation, the base reservoir can be further formed with one or more capture latch elements that can cooperate with one or more features of the diffuser to releasably latch and capture the diffuser in the reservoir base.

As those skilled and knowledgeable in the relevant and related arts may be able to further contemplate, the preferred and alternative configurations of the embodiments of the present invention are also further susceptible to a nebulization system that is adapted for use with a variety of previously characterized preselected substances whereby a plurality of calibrated and interchangeable diffusers is fabricated for use with a single effluent vent cap and multiply configured reservoir bases each calibrated to accept a predetermined amount or quantity of the preselected substance or a continuous supply thereof for delivery at a predetermined rate of flow.

These variations, modifications, and alterations of the various preferred and alternative embodiments and configurations may be used either alone or in combination with one another as can be better understood by those with skill in the art with reference to the following detailed description of the preferred embodiments and the accompanying figures and drawings.

BRIEF DESCRIPTION OF THE DRAWINGS

Without limiting the scope of the present invention as claimed below and referring now to the drawings and figures, wherein like reference numerals, and like numerals with primes, across the several drawings, figures, and views refer to identical, corresponding, and or equivalent elements, components, features, and parts:

FIG. 10 is a plan top view of a diffuser, rotated and in enlarged scale, of the nebulizer of FIG. 1 to 3 and which is specifically depicted in FIG. 2;

FIG. 11 is a front view, in enlarged scale and rotated, of the diffuser of FIG. 10;

FIG. 12 is an underside view of the diffuser of FIGS. 10 and 11;

Figure 1:
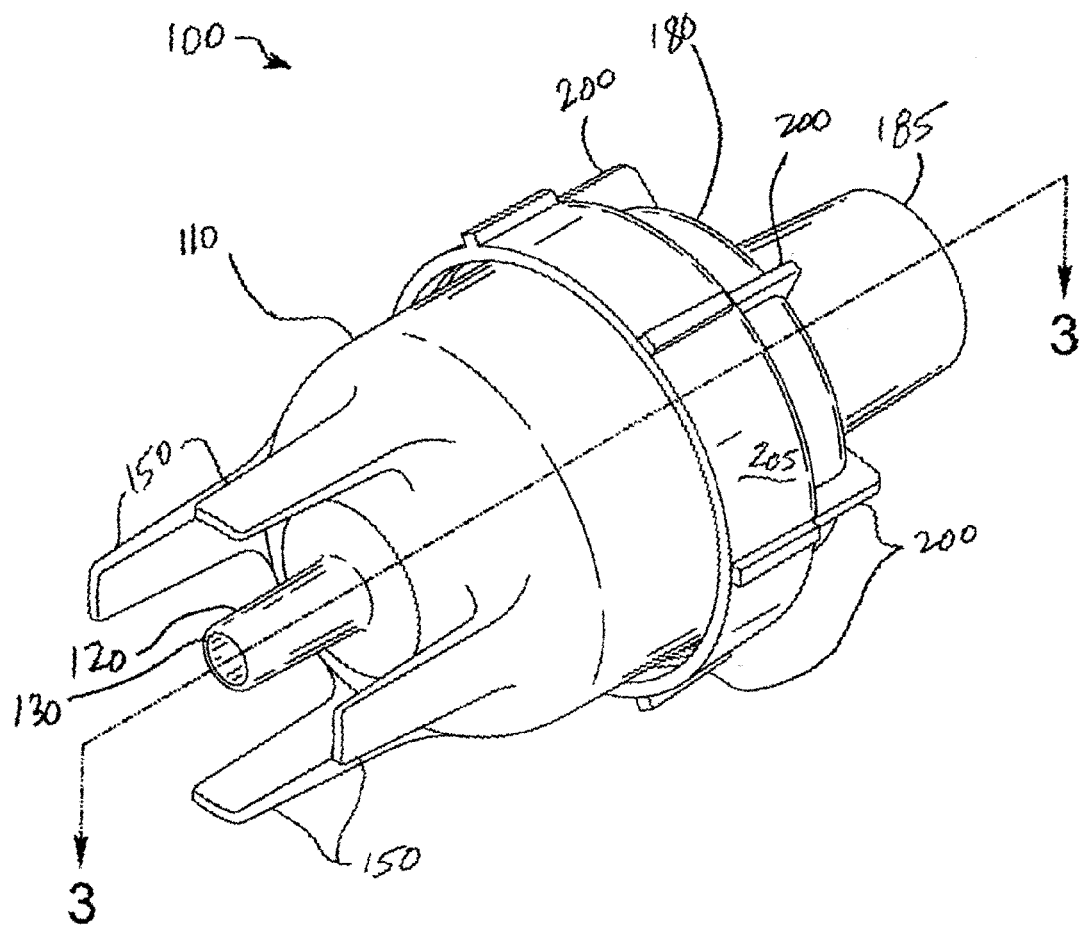
FIG. 1 is an elevated isometric perspective view, in enlarged scale, of a small volume nebulizer according to the principles of the present invention.

Also, in the various figures and drawings, reference symbols and letters are used to identify significant features, capabilities, dimensions, objects, and arrangements of elements described herein below in connection with the several figures and illustrations.

DESCRIPTION OF THE SPECIFIC EMBODIMENTS

Pulmonary inhalation therapies have long been employed as a means to quickly introduce generally small volumes of highly efficacious substances and medicaments to a patient in situations where other therapeutic regimens can be less desirable. One of the most prominent indications and symptoms that are preferably treated using various inhalation techniques include asthmatic and other respiratory distress maladies. Other equally important therapies that are preferably employed using inhalation therapies are those where ordinary vascular infusion via injection is undesirable due to infection risks, vascular deterioration and distress, and medicament incompatibility with direct vascular infusion techniques, and in situations where oral ingestion creates problems in regard to patient comfort and well-being, gastrointestinal physical and biochemical distress, and medicament efficacy loss or incompatibility with the gastrointestinal environment. Various inhalation techniques and devices have been developed over the many years since its use was first initiated and many considerations exist to assist in discerning the most appropriate therapeutic approach.

For any of a number of ailments or illnesses, heat or ultrasonically induced vaporization of a liquid or liquid-borne fine particulate treatment substance is indicated to supply a vapor to a patient who will inhale or inspire such for purposes of affecting the prescribed treatment regimen. However, those with knowledge in the relevant technology have come to appreciate that such vaporization techniques can be unduly wasteful and unpredictable in many instances. These problems are primarily due to the likelihood that, under nominal breathing circumstances, much of the inhaled vapor is not absorbed or otherwise retained within the pulmonary or respiratory tract of the patient. Instead, much of the inhaled vapor is immediately expelled as the patient exhales normally. This is primarily because, among other reasons, the vaporized treatment substance consists of extremely fine sub-micron sized particles that are easily exhaled by the patient and retained in the pulmonary tract.

In contrast to vaporization techniques, sometimes similar misting techniques can employ heat, forced air, sprayed, and ultrasonically induced mists, which while similar in many respects to vaporization methods and related devices, supply a mist of droplets that are usually far larger than those in the vaporization applications. Such misted particles or droplets often can range between about 100 μM and 500 μM, and far larger. Droplets or particles of this size usually will rarely reach beyond the upper respiratory tract of a patient and may impinge and come to rest in the respiratory tract superior to the epiglottis such that the treatment substance or medicament will find its way into the gastrointestinal tract instead of the pulmonary tract.

In further contrast to the preceding therapeutic techniques, atomization or what has commonly come to be known as nebulization has been demonstrated to be among the most advantageous of the various inhalation techniques for therapies that require dispersion of the treatment substance or medicament into the tracheobronchial and lung parenchyma, the target sites for many medicaments, as well as the alveolar air passageways of the pulmonary system. Even so, current nebulization techniques and related devices or nebulizers have many complexities and thus far been unable to offer easily controlled treatment regimens wherein specific quantities of preselected treatment substances and medicaments can reliably, predictably, and reproducibly be inhaled by the patient efficiently and without undue complexities or economic burdens. Such needs remain especially poignant given that atomization and nebulization therapies have the potential to be among the best for wide-scale pulmonary tract treatments, and for instant absorption of a small volume of medicament in smaller relative local concentrations within the vascular system, which avoids unduly high concentrations in any one vascular vessel, among the many other possible benefits.

Some individuals having skill in the related arts of nebulization technology have found that maximum therapeutic effects from nebulized inhalants can be achieved when the preselected therapeutic agent, treatment substance, or medicament is entrained in an inhaled fluid or air stream and to have a droplet or particle size in the range of between about 1 μM and 5 μM. See, for example, Hendric, Design Characteristics of Drug Nebulizers, *J. Medical Engineering and Technology*, 16 (1992) 63-66. Various manufacturers of a wide variety of medicaments that are adapted for aerosol or nebulizer inhalation treatment regimens have established that certain medications are best suited to and can require alveolar deposition, which requires that the inhaled medication have a droplet or particle size in the inspirable range of between about 1 μM and 3 μM. Other medications are better suited for and even indicated for tracheobronchial or lung parenchyma deposition, which optimally would require a medicinal droplet or particle size in the range of between about 2 μM to 5 μM.

Figure 2:
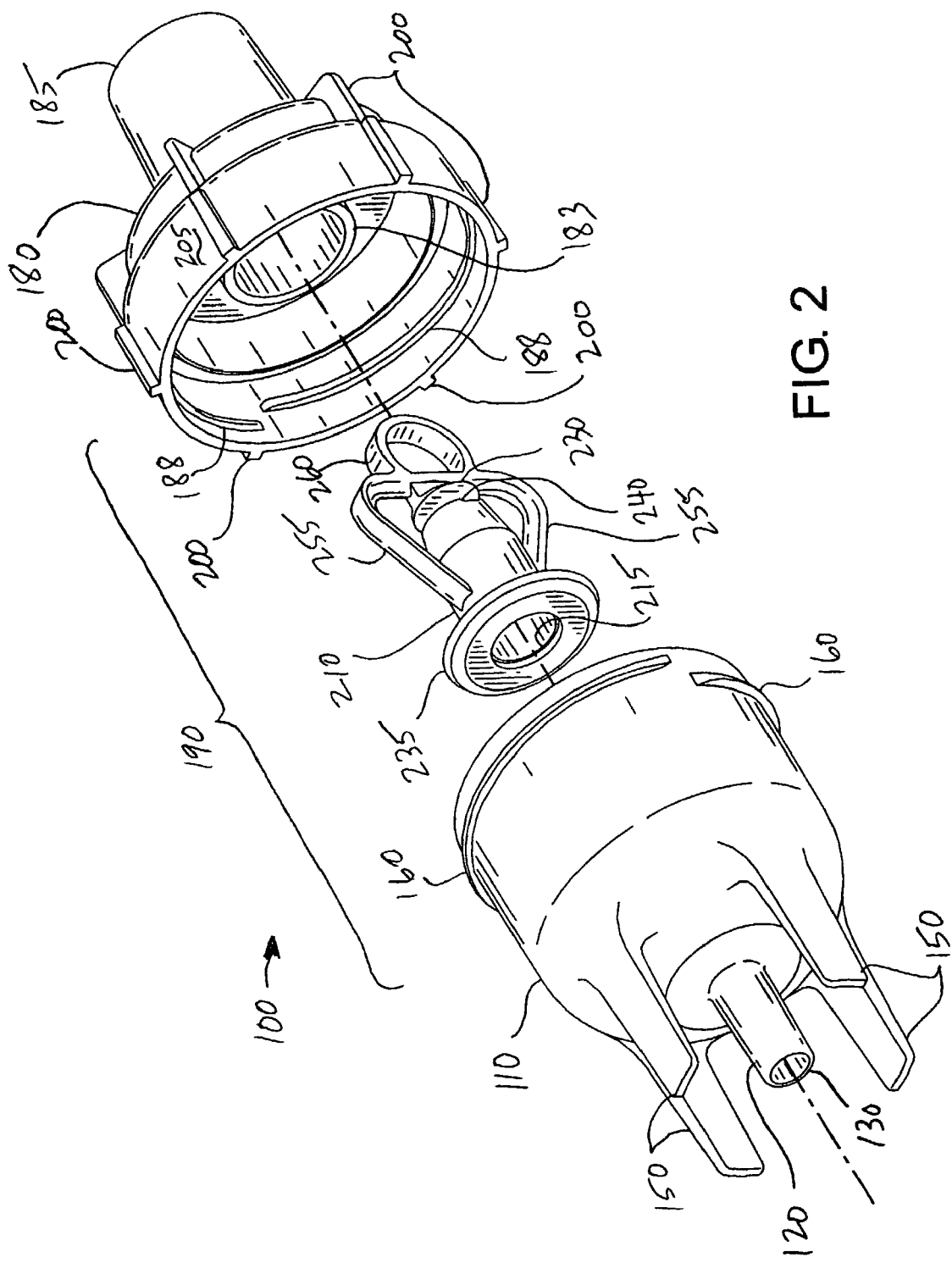
FIG. 2 is an elevated isometric exploded view of the nebulizer of FIG. 1.
Figure 3:
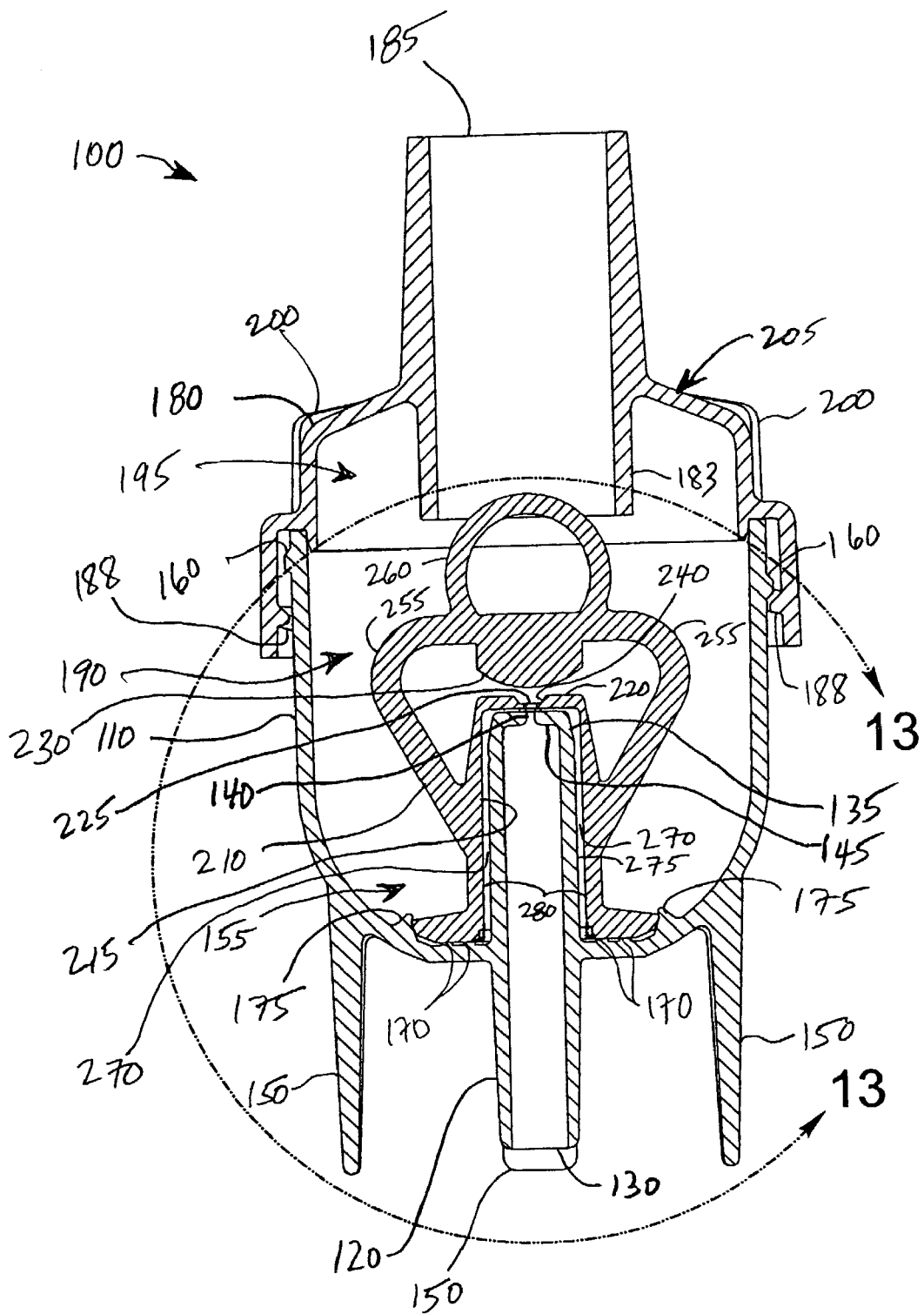
FIG. 3 is a section view, rotated and in enlarged scale, taken approximately about section line 3-3 through the nebulizer of FIG. 1.

With these considerations in mind, those skilled in the art will come to understand that the present invention offers a number of possible configurations that can selectively and predictably control the droplet or particle size for the widest possible range of preselected treatment substances and therapies with high efficiency, optimized efficacy, reproducibility, and without undue expense or complication. With reference to the various figures and specifically with reference now to FIGS. 1, 2, and 3, a small volume nebulizer 100 according to the principles of the present invention is depicted.

In a first of many possible configurations, the nebulizer 100 incorporates a reservoir base 110 that is sized to receive a predetermined quantity of the preselected treatment substance. Although many possible sizes are contemplated for purposes of the contemplated nebulizer 100, in the depicted small volume nebulizer 100 it is anticipated that the base reservoir 110 will be preferably sized to receive in the range of approximately between about 1 mL and 50 mL of the preselected treatment substance, and more preferably between about 1 mL and 30 mL, and even more preferably between about 5 mL and 20 mL.

Figure 4:
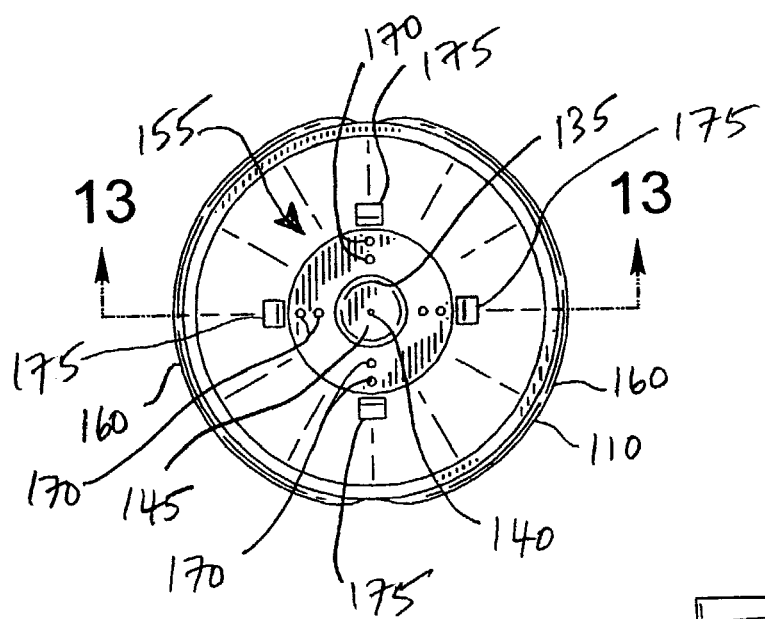
FIG. 4 is a top plan view of a reservoir base, rotated and in enlarged scale, of the nebulizer shown in FIGS. 1 to 3.
Figure 5:
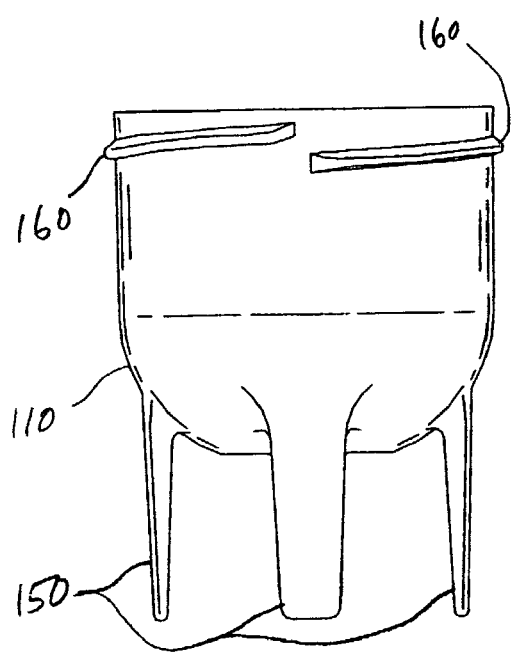
FIG. 5 is a side view, rotated and in similar scale, of the reservoir base of FIG. 4.
Figure 6:
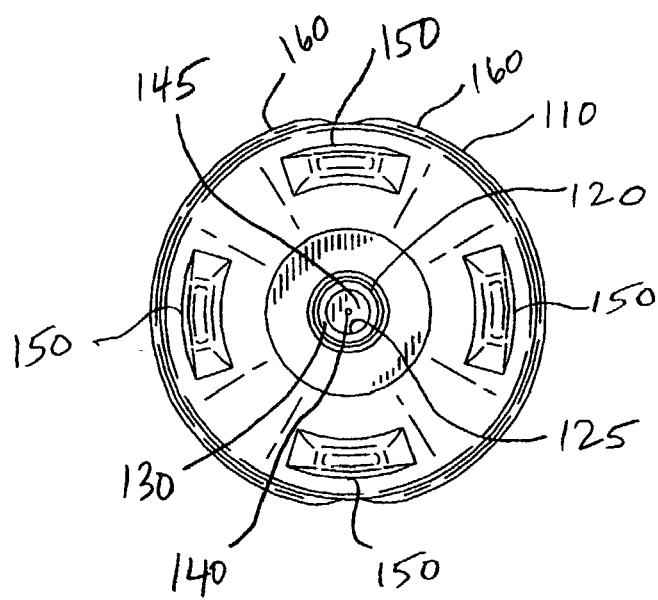
FIG. 6 is an underside view, in similar scale, of the reservoir base of FIGS. 4 and 5.

With continued reference to the various figures and also now to FIGS. 4, 5, and 6, the reservoir base 110 is also preferably formed with a pressurized fluid inlet tube 120 that is adapted to be attached to a pressurized or compressed air or fluid source such as those commonly found in nearly every American hospital room. So that the pressurized air or fluid stream can be accelerated to have an increased velocity, the inlet tube 120 is formed with in internal fluid passageway 125 that has a decreasing internal taper in the direction of the desired fluid flow from an inferior end 130 to a distal superior end 135. The inlet tube terminates at the distal superior end 135 with a distal metering orifice 140 that is adapted to regulate the flow of the fluid therethrough. A distal end wall 145 that defines the entrance and exit of the metering orifice 140 is preferably minimized in its thickness dimension to reduce the deceleration and energy loss of the fluid as it passes through and across the edges of the wall 145, which edges define the periphery of the orifice 140. Such deceleration is due to, among other reasons, the sidewall frictional losses and side turbulence resulting from random boundary layer separation of the fluid stream along the walls of the orifice 140.

The reservoir base 110 also may be optionally formed with at least one and optionally four downwardly projecting support members 150 that can preferably be integrally formed as part of or that can be otherwise attached to the reservoir base 110. As depicted in the various views and drawings, the support members may generally be downwardly projecting legs or support members 150. However, many other types of support members are possible as herein further described, and all of such are adapted to establish a free-standing capability of the nebulizer 100 when it is placed upon a substantially level surface for purposes of filling with or measuring the preselected substance (not shown).

In various other alternative arrangements, a different support member (not shown but within the skill of those knowledgeable in the arts) may be formed as a downwardly facing surface or projecting rim that could be analogous to an upside-down water or drinking glass, and which would similarly support the proposed reservoir base 110. As depicted in the various figures, the reservoir base 110 is illustrated to have a lofted ellipsoid or ovoid profile that establishes a pooling of the preselected treatment substance in a lower vessel 155. This ovoid surface profile is best suited to freely stand at rest in an upright position on a level surface with the added support members or legs 150 act to stabilize the base 110, or with some other similarly capable modification to the profile surface or with use of a companion stand device to improve free-standing capability.

In still other variations of the base reservoir 110, one or more coupling devices may be incorporated, such as threads 160. Although not depicted in the figures, a range of other equally suitable coupling devices are available including for purposes of example without limitation, twist-lock elements, bayonet fittings, press and friction fit snap on latches like those used to secure caps to medicine bottles, or any other of a variety of coupling mechanisms and components that could be similarly capable to releasably couple the base 110 to other components.

As before, the present embodiment of the reservoir base 110 may be further modified to include anti-siphoning features to prevent leakage and loss of the potentially costly preselected treatment substance when the proposed nebulizer 100 is in use at less than optimal orientations. A useful anti-siphoning capability compatible for use with the preferred nebulizer 100 can include the base reservoir 110 being adapted with the pressurized fluid inlet tube 120 projecting up and into the base reservoir 110 sufficiently far so that the superior end 135 of the inlet tube 120 terminates at a distance above the highest contemplated top surface (not shown) of the preselected substance when the reservoir base 110 is filled to capacity. In this and a variety of similarly effective ways, the preselected treatment substance can be prevented from escaping into the inlet tube 120, which can result in the substance being siphoned out of the reservoir base 110.

Although reflected in the various figures to be generally cylindrical in its exterior profile, the inlet tube 120 may be adapted to have any of a number of equally suitable cross-sectional profiles that can include, for example without limitation, cuboid and polygonal profiles (not shown). Other features that can be incorporated into the inlet tube 120 can include, for further non-limiting illustrative example, key and rail features that can enhance alignment capabilities with other components and that can be adapted to cooperate with corresponding elements therein such as keyways and raceways and the like.

The present invention also contemplates yet additional alternative and optional modifications and variations of the illustrated embodiments wherein various additional optional features are incorporated on reservoir base 110. For example, the reservoir base 110 can include, about an interior surface 165 that establishes a bottom or floor surface of the lower vessel 155, one or more standoffs 170 that can be shaped, sized, and positioned to optimize a capillary interstice 270 that is formed as further described herein. On interior or exterior walls of the reservoir base 110, various volumetric indicia can be imprinted or otherwise formed to establish measurement capabilities that may be useful and desirable during setup, operation, and refilling of the nebulizer 110. Such indicia, although not shown in the figures, can include unit dimensions of volume such as "CCs" and milliliters and ounces, and similar such designations.

In yet additional optional alternative arrangements, wherein it is desirable to releasably secure other components to the reservoir base 110 in a way that communicates positive tactile feedback to the operator during setup and operation, the base reservoir 110 can be further formed with one or more capture latch, securing or holding elements 175 that can cooperate with one or more features of the other components to releasably latch, secure or hold them to the reservoir base 110.

Figure 7:
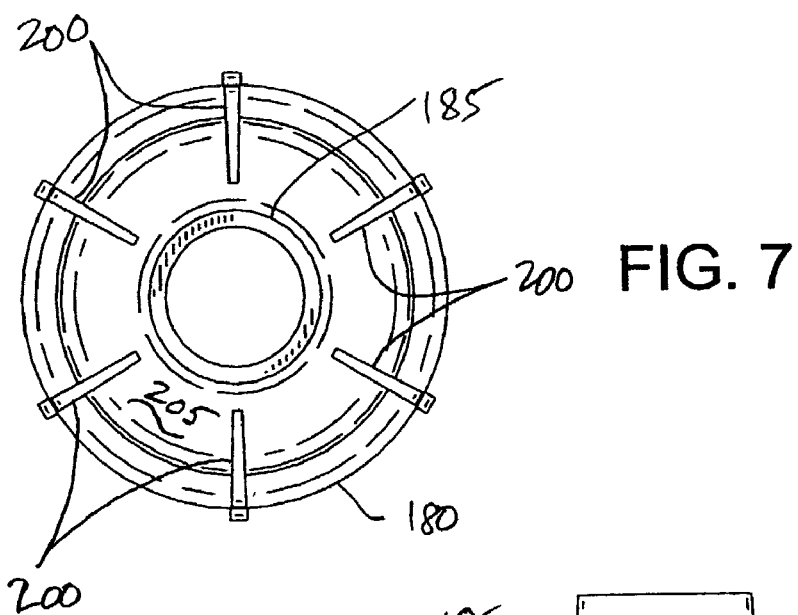
FIG. 7 is a plan top view of an effluent vent cap, rotated and in enlarged scale, of the nebulizer of FIGS. 1 to 3.
Figure 8:
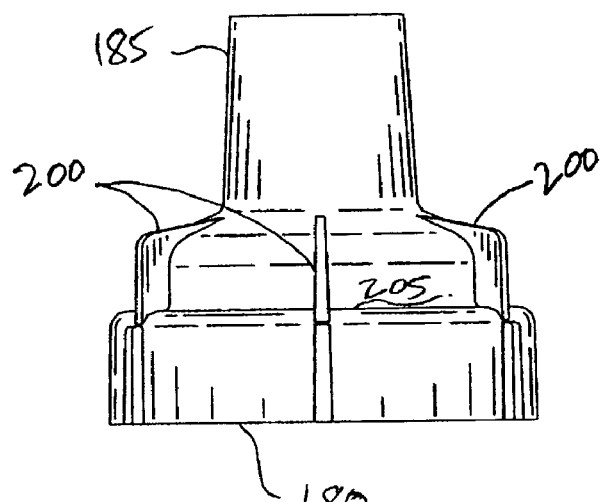
FIG. 8 is a side view of the effluent vent cap depicted in FIG. 7.
Figure 9:
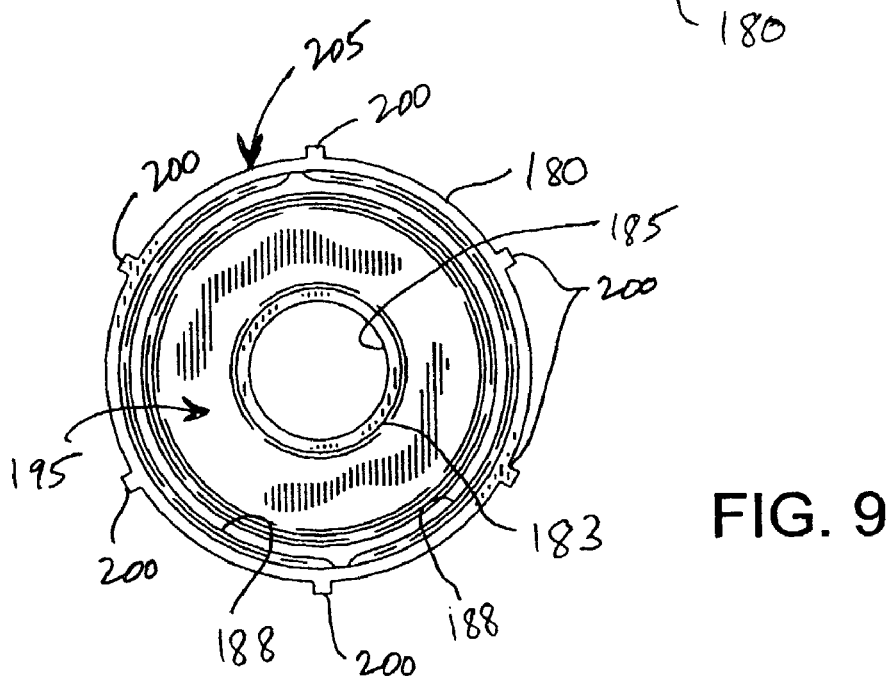
FIG. 9 is an underside view of the effluent vent cap of FIGS. 7 and 8.

With continued reference to the previously described illustrations and now also to FIGS. 7, 8, and 9, the preferred nebulizer 100 also includes an effluent vent cap 180 that is preferably formed with an aerosol outlet 185. The effluent vent cap 180 is preferably configured to be removably coupled to the reservoir base 110 to form an interior cistern 190 with an upper recess 195 and the lower substance storage vessel 155. The effluent vent cap 180, similar to the reservoir base 110, is also preferably adapted with threads 188, or twist-lock elements, or any other of a variety of coupling mechanisms and components compatible for use in coupling to the corresponding threads 160 or other contemplated coupling devices of the reservoir base 110. Any of the preceding configurations are also compatible for incorporating handling and twist grips 200 that may be formed integrally about an exterior surface 205 of the effluent vent cap 180.

In yet additional modifications and variations to the specific embodiments described herein, the aerosol outlet 185 of the effluent vent cap 180 may be further optionally or preferably formed with a baffle lumen 183 that can be adapted to project interiorly into the upper recess 195. This modified configuration to the effluent vent cap 180 will lengthen the path a particle that is entrained and traveling in the effluent fluid or air stream must travel after being deflecting off of the dispersing baffle or baffle disperser 230. The lengthened path will increase the likelihood that oversized droplets or particles will be recaptured and renebulized instead of exiting nebulizer 100 so as to minimize waste and improve the overall efficacy of the nebulized treatment substance or medicament to be inhaled by the patient. The baffle lumen 183 may be even further lengthened or changed in shape, pathway, diameter, to have further baffle features so as to establish an anti-siphon and or anti-leak capability similar to that contemplated by and described in connection with the uptake lumen or channel 215, which additional capability of the effluent vent cap 180 can improve the capability of the nebulizer 100 to be used in unusual orientations.

When coupled or joined together, the reservoir base 110 and the effluent vent cap 180 positively capture an interchangeable diffuser 210. As can be better understood with continued reference to the various drawings and now also specifically to FIGS. 10, 11, and 12, the preferred interchangeable diffuser 210 can be one of a plurality of such diffusers that are each adapted and optimized for a particular treatment regimen and or a particular one of a plurality of possible preselected treatment substances. More specifically, such additional diffusers, which may be similar or analogous in configuration to diffuser 210, can be specifically adapted so as to establish a desired rate of nebulization, a preferred droplet or particle size and or a preferred quantity of such droplets or particles for each such substance or each such treatment regimen. In another embodiment of the present invention, diffuser 210 may not be interchangeable but instead can be made as part of the reservoir base 110.

Figure 13:
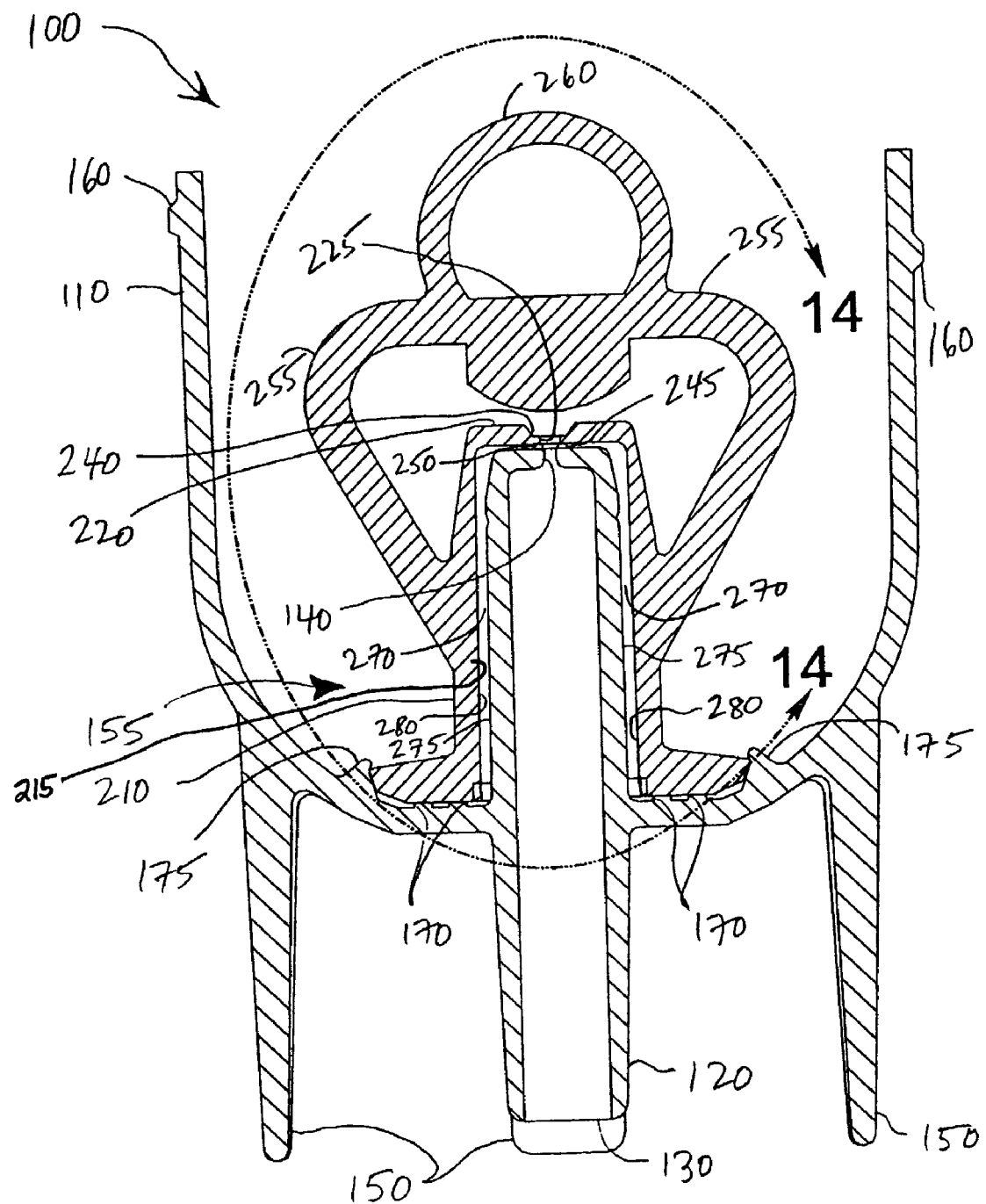
FIG. 13 is a detail section view of the nebulizer of FIGS. 3 and 10 taken approximately about detail line 13-13 of FIG. 3 and section line 13-13 of FIG. 4, and rotated and in enlarged scale and with certain structure removed for purposes of clarification.
Figure 14:
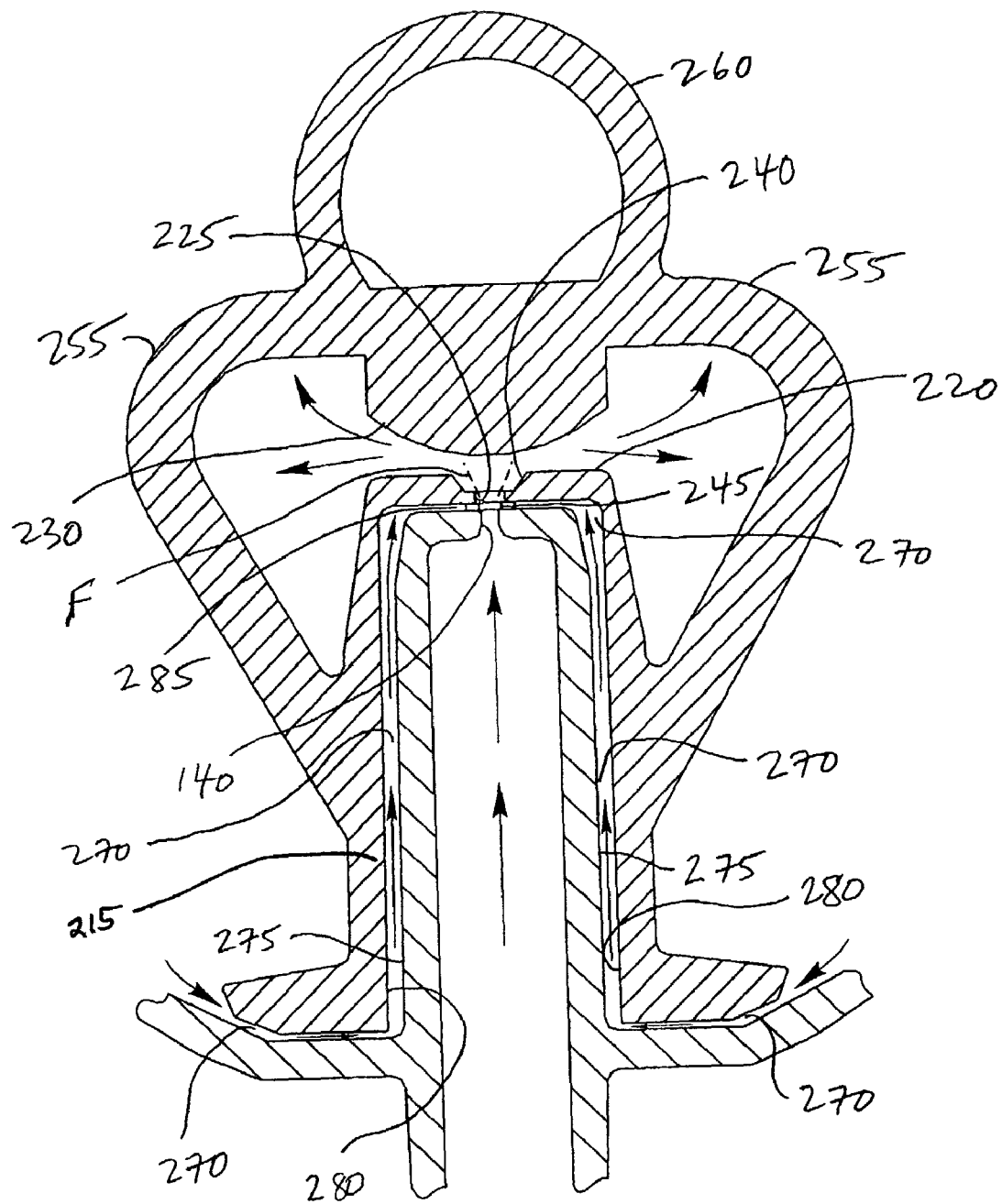
FIG. 14 is a detail view taken generally about section line 14-14 of FIG. 13, in enlarged scale and with various structure removed for further purposes of illustration.

With reference now also to FIGS. 13 and 14, and with continued reference to the previously noted figures, it can be understood that the diffuser 210 is ideally formed with an uptake lumen or channel 215 that is adapted to receive and be seated upon the inlet tube 120 whereby, during operation, the lumen or channel 215 is in fluid communication with the preselected substance that is to be contained in the lower vessel cistern 155. The lumen or channel 215 preferably terminates at a superior end bulkhead 220 that is formed with a nozzle jet 225. The nozzle jet 225 is operative to spray a jet of fluid F (FIG. 14) against an integrally formed dispersing baffle or baffle disperser 230 that is positioned in a superior, axially aligned position proximate to the nozzle jet 225. When the uptake lumen or channel 215 is received with and seated about the inlet tube 120, the nozzle jet 225 of the diffuser 210 is preferably axially aligned with and superiorly proximate to the distal metering orifice 140 of the inlet tube 210.

Although many possible configurations are possibly with the new and novel embodiments and configurations of the present invention, it has been demonstrated that the nozzle jet 225 can preferably have a cross-sectional area that is approximately larger than that of the distal metering orifice 140, which in operation and in combination with the other features and components described herein, creates a suitably capable jet spray pattern F (FIG. 14) that will impact upon the dispersing baffle 230 to disperse and atomize the preselected treatment substance into desirably sized droplets or particles to establish the nebulized effluent aerosol.

The precise position, size, shape, and orientation of the dispersing baffle 230 is selected and arranged for purposes of dispersing the sprayed jet of fluid F to establish the desired mean average diameter of the resultant droplets or particles, which is a further function of the particular preselected substance or medicament and the prescribed treatment regimen. Preferably or optionally, the illustrated dispersing baffle 230 may be sized in its lateral or side-to-side dimension to be larger than the effluent spray pattern F (FIG. 14) so that the droplets or particles from the spray stream pattern F being ejected from the nozzle jet 225 are obstructed and deflected and can not move in a straight line towards the aerosol outlet 185 of the effluent vent cap 180.

Instead, only droplets or particles small enough to be carried around the dispersing baffle 230 will exit in this manner. The majority of all other larger and undesirably oversized droplets or particles, whether directly emitted from the nozzle jet 225 or deflected from the dispersing baffle 230, will impact the interior walls 167 and drain back into a pool in the lower vessel 155, or they will fall under force of gravity into the pool of the preselected treatment substance or medicament.

Although the dispersing baffle 230 is depicted to be generally circular and somewhat concave in cross-section, many other profiles are possible that can be similarly capable of creating the desired nebulized droplets or particles having the preferred mean average diameter profile. For further examples, rectilinear and pyramidal and other non-circular and non-concave shapes and profiles are contemplated as having application for purposes of the present invention. Similarly, even though the various figures illustrate the orifice 140 and the nozzle 225 to be defined as generally circular, those skilled in art can understand that many other noncircular configurations are possible, which alternative arrangements can establish various spray patterns and which can cooperate with many variations of possible dispersing baffles including baffle 230 to thereby establish the desired nebulization rates and spray pattern characteristics.

The uptake lumen or channel 215 is shown in the various drawings and illustrations to be generally cylindrically shaped. However, the present invention contemplates a wide range of possible shapes for lumen or channel 215 that preferably correspond with the size, shape, and cross-sectional profile of and so as to receive the inlet tube 120. Additionally, although not shown in the figures, the uptake lumen or channel 215 can optionally or preferably incorporate other elements and features that can offer alignment capability such as keyways and raceways that can cooperate with corresponding features on the inlet tube 120. Such additional features may also include, for purposes of further illustration but not limitation, one or more distal end ribs 245 that are adapted to standoff the diffuser 210, when received with and seated upon the inlet tube 120, from the distal superior end 135 of the tube 120 to define a vacuum space and interstice as further illustrated herein.

Further, the uptake lumen or channel 215 also may incorporate one or more side wall ribs 250 that are adapted to seat, center, and precisely align the diffuser 210 relative to the received inlet tube 120 so that the nozzle jet 225 and the orifice 140 are coaxially aligned and registered with one another and so as to establish the interstice described in detail elsewhere herein. This arrangement can also help the capillary action. Although the figures depict the distal end ribs 245 and side wall ribs 250 to be three in number and radially spaced apart, those skilled in the art should recognize that single, double, and larger numbers of such analogous and alternately arranged and modified elements can be incorporated to establish similar capabilities and configurations.

The preferred interchangeable diffuser 210 according to the present invention may also further include one or more arcuate baffle arms 255. Such baffle arms 255 are preferably adapted to maintain the desired orientation and position of the dispersing baffle 230 relative to the nozzle jet 225 so as to maintain consistent nebulization of the preselected substance regardless of how many times the diffuser 210 may be modified and or interchanged with alternately configured diffusers, and irrespective of the how often the nebulizer 100 may opened, refilled, cleaned, and or reused. The various figures illustrate that two baffle arms 255 are integrally formed with the diffuser 210. Even so, it should be understood that one or more such arms 255 may be included and that the arms 255 may be further adapted to have various other shapes and profiles and to be further adapted with additional features that can operate themselves as secondary, tertiary, and or quaternary baffles to cooperate with the primary dispersing baffle 230 in dispersing and breaking up the droplets and particles to have the desired mean average diameter that is most preferred for a given preselected treatment substance or therapeutic treatment regimen.

Additionally, such baffle arms 255 may incorporate a diffuser handle 260 adapted to increase the ease with which the user may remove, replace, and interchange the diffuser 210 with other diffusers that may be optimized for a different set of nebulization parameters (such as a different preferred droplet or particle size and quantity) or for use with a different preselected treatment substance. Further, even though only one loop-type handle 260 is shown, many other suitable handle arrangements can be incorporated with equally effective results.

The preferred diffuser 210 also may further incorporate a footer disc 235 at a lower extremity that can be adapted, among other capabilities described herein, to cooperate with the capture latch elements 175 of the reservoir base 110 to releasably secure the diffuser 210 thereto in a positively aligned and latched or secured orientation. Additionally, the cooperative capability of the footer disc 235 and capture latch elements 175 can be further adapted to induce a snap-click type of positive tactile feedback to the user to signal that the diffuser 210 is properly seated against, aligned to, and received with the inlet tube 120.

In any of a number of possible variations, alternatives, and modifications of the embodiments disclosed herein and contemplated for use with the present invention, the jet nozzle or nozzle jet 225 of the diffuser 210 may also further incorporate at least one diverging spray guide, channel, or groove 240 that is configured to optimize the divergence pattern F of fluid being sprayed from the nozzle jet 225.

The optional or preferred diverging spray guide, channel, or groove 240 can be implemented wherein the jet nozzle 225 is formed in the superior end 220 or bulkhead of the uptake lumen or channel 215 such that the end bulkhead 220 is further formed to have a substantially lateral channel 240 that is defined by at least two generally confronting and parallel or askew sidewalls 265. The lateral channel 240 configuration is preferably substantially registered and optionally centered about the jet nozzle 225 to serve at least two or more distinct and complementary functions. Most prominently, the channel 240 minimizes the thickness of the end bulkhead 220 proximate to the nozzle 225, which reduces the head or pressure losses due to friction and turbulence, among other energy drains, of the fluid moving through aperture of the nozzle jet 225 along the side walls 265. Next and just as importantly, the sidewalls 265 are configured to control the divergence of the fluid stream pattern F being sprayed from the jet nozzle 225.

The sidewalls 265 are configured about the exit plane of the nozzle jet 225 to define an angle relative to the net velocity vector of the fluid stream and or to each other.

While the relative angle has been found to be variably dependent upon the type of sprayed or flowing fluid, as well as the temperature, the viscosity, and the pressure differentials across the various elements, among other parameters, the relative angle between side walls 265 of preferably in the range of between about 5 and 47 degrees has been found to establish an optimized and efficient spray pattern F and fluid stream for nebulizer 100 of the present invention, and has been further demonstrated to be compatible for use with a wide variety of the more commonly contemplated therapeutic treatment regimens and preselected treatment substances and medicaments.

The preferred diffuser 210 of the present embodiments is also further adapted to cooperate with the interior walls 167 and or the interior surface 165 of the reservoir base 110 such that, when the uptake lumen or channel effluent 215 is seated against, aligned to, and received with the inlet tube 120, a capillary interstice 270 is formed between an exterior surface 275 of the inlet tube and the confronting interior surface 280 of the uptake lumen or channel 215.

When the liquid preselected treatment substance or medicament is in fluid communication with a lower or inferior region of the capillary interstice 270, the force of adhesion between the treatment substance or medicament is preferably greater than the force of cohesion inherent in the treatment substance or medicament such that it is drawn up into the interstice 270 by capillary action. Certain types of such preselected treatment substances or medicaments can be further formulated so as to enhance or diminish the effect of capillary action as may be required for purposes of the present invention, treatment therapies, or particular treatment substances of interest. As noted elsewhere herein, such capillary action may also be enhanced or diminished or precluded by selection of suitable materials for the construction of nebulizer 100 or by treatment of the surfaces of such materials, or both.

Additionally, when the lumen 215 and the inlet tube 120 are so joined, the proximately registered and coaxially aligned nozzle jet 225 and the distal metering orifice 140 operate to define a vacuum space 285 (FIG. 14) that is in fluid communication with the distal orifice 140 and the capillary interstice 270. During operation wherein pressurized fluid is being sprayed through the orifice 140, through the vacuum space 285, and through the nozzle jet 225, the moving and diverging fluid stream and spray pattern creates a pressure drop that develops the vacuum, relative to the ambient atmospheric pressure outside the nebulizer 100, in the vacuum space 285. Thus, it can been seen that the preselected treatment substance or medicament is thereby also drawn into the interstice 270 and into the vacuum space 285 under the force of the developed vacuum to be put into contact with the fluid stream exiting the metering orifice 140. Thus, under the force of either capillary action or the vacuum pressure differential or both, the uptake of the preselected treatment substance can be further regulated.

Once the treatment substance comes in contact with the spray stream pattern exiting the metering orifice 140, the substance will be dispersed by shearing action, among other forcing functions, into droplets or particles that may have a mean average diameter or size in the range of about 10 $\mu M$ to 500 $\mu M$. The sprayed fluid stream is contemplated herein to preferably be an air stream, but the present invention is also suitable for use in applications where certain other fluid streams may be used.

Once preliminarily broken up into droplets or particles, the dispersed droplets or particles present in the vacuum space 285 become entrained in the exiting air or fluid stream and are accelerated and sprayed in a spray pattern such as pattern F (FIG. 14) through the nozzle jet 225 where they then impact the dispersing baffle 230. The kinetic energy of the impact breaks apart the droplets or particles into smaller such droplets and particles that are deflected into the air or fluid stream that is moving around the dispersing baffle 230. The majority of those droplets or particles having a sufficiently small size are entrained in the air or fluid stream and carried out of the nebulizer 100 through the aerosol outlet 185. The majority of the other over-sized droplets and particles are recaptured into the pool in the lower vessel 155 and redrawn into the interstice 270 to be reatomized.

One or more of the components of the nebulizer device 100 of the present invention can be fabricated from a polymer material that is known to be compatible for use with the largest possible range of contemplated applications and preselected substances. Also, the preferred material can be selected for use in special purpose applications and environments as may be desirable or otherwise required. Such polymers that are preferred for purposes of the contemplated nebulizers illustrated herein are most commonly selected from the group of materials that includes, for purposes of use with any of the preferred and alternative embodiments without limitation, glass, ceramics, metals, thermoset and elastomer monomers and polymers, and monomeric and polymeric thermoplastics including, for further purposes of illustration but not for purposes of limitation, thermoplastics selected from any of a variety of commercially available and suitable materials including acetal resins, delrin, fluorocarbons, polyesters, polyester elastomers, metallocenes, polyamides, nylon, polyvinyl chloride, polybutadienes, silicone resins, ABS (acrylonitrile, butadiene, styrene), polypropylene, liquid crystal polymers, alloys and combinations and mixtures and composites thereof, and reinforced alloys and combinations and mixtures and composites thereof.

There are a variety of suppliers of such polymeric compounds available and one such supplier includes Dow of Midland, Mich., USA, a manufacturer of virgin and recycled polystyrene and other polymeric compounds, and who specifically can supply a variety of crystal polystyrenes among other types of possibly suitable materials. Such supplied polymers can differ from one another in their thermal, optical, and other properties and can be selected to accommodate a wide range of preferred characteristics as may be needed or desirable for particular applications of the preferred and optional embodiments of the nebulizer 100 according to the present invention. For purposes of further examples, the United States Department of Health and Human Services via the Food and Drug Administration has designated and identified various possibly suitable materials as in Title 21 of the United States Code of Federal Regulations (CFR) Parts 170 through 199 and parts 800 through 1299.

In order to establish the optionally desirable increase or attenuation in capillary action within the interstice 270, and depending upon the particular preselected treatment substance(s) and the material(s) that may be selected for fabrication of the various nebulizer 100 components contemplated herein, it is possible to selectively control the affinity and surface energy properties of the surface of the substrate of the material used for the components of nebulizer 100 by inducing increased adhesion forces between the materials of the capillary interstice and the preselected treatment substance(s). The surface energy of the material can be adjusted among other means by establishing polarized regions on the polymer chains of the substrate.

One example of this technology is the treatment of ordinarily hydrophobic polystyrene, for example, to render its surface hydrophilic, which can increase its adhesive affinity for various possible preselected treatment substances. One possible type of selective binding control includes plasma treatment, which exposes the target surfaces to, among other possible plasma constituents, energized electrons, protons, neutrons, and molecules such as ions, free radicals, and others. More commonly, processes including corona discharge or flame treatments can be used to generate the plasma needed for treating polymer surfaces. Corona discharge involves the application of a high frequency, high voltage signal from an electrode, across an air space or gap, through the polymer substrate to the surfaces to be treated and then to some dielectric material.

If corona discharge or conventional plasma treatments are not desirable, convenient, or compatible with a particular polymeric substrate, a gas flame treatment can also be used to effect the plasma treatment. Like corona discharge, this type of treatment increases the surface energy of the substrate and can render it hydrophilic, and can in certain configurations improve the capillary action of the polymer surface. In addition to these possible treatments, those skilled in the art may also further appreciate that alternative treatments are also contemplated wherein an additional layer of film or a substance applied as a film is incorporated onto the substrate surface to increase or attenuate the capillary action capability. For example, a hydrophilic or partially hydrophilic, that is an amphipathic protein can be applied to the untreated, hydrophobic polymer surface to be treated, which can be useful for compatibility with various nebulization applications and preselected treatment substances.

Numerous alterations, modifications, and variations of the preferred embodiments disclosed herein would be apparent to those skilled in the art and they are all contemplated to be within the spirit and scope of the present invention, which is limited only by the following claims. For example, although specific embodiments have been described in detail, those with skill in the art can understand that the preceding embodiments and variations can be modified to incorporate various types of substitute and/or additional materials, relative arrangement of elements, and dimensional configurations for compatibility with the wide variety of possible preselected treatment substances and medicaments that are available in the marketplace. Accordingly, even though only few embodiments, alternatives, variations, and modifications of the present invention are described herein, it is to be understood that the practice of such additional modifications and variations and the equivalents thereof, are within the spirit and scope of the invention as defined in the following claims.

What is claimed is:

1. A nebulizer, comprising:
    a reservoir base formed with an inlet tube and adapted to receive a substance to be dispensed, the inlet tube incorporating an orifice about a distal end of the tube;
    an effluent vent cap formed with an aerosol outlet and being removably secured to the reservoir base thereby defining an interior cistern with an upper recess and a lower substance storage vessel for containing the substance;
    an interchangeable diffuser optimized to nebulize the substance, said diffuser being not directly connected to the vent cap, being releasably held within the cistern, and being formed with an uptake lumen having at one end a jet nozzle, the lumen configured to be removably engaged about the inlet tube to form a capillary interstice and to axially register the jet nozzle proximate to the orifice establishing a vacuum space therebetween;
    wherein the diffuser further includes an integral baffle disperser substantially axially aligned superior to the jet nozzle and configured to deflect and nebulize particles of the substance traveling along a path passing through the orifice and the jet nozzle;
    wherein, when the diffuser is held within the cistern, the orifice of the inlet tube is stationary relative to the jet nozzle, and
    wherein the aerosol outlet of the effluent vent car is further formed with a baffle lumen projecting interiorly into the upper recess.

2. The nebulizer according to claim 1, wherein the diffuser is adapted for releasable engagement to the reservoir base to establish a precise arrangement of the jet nozzle relative to the orifice of the reservoir inlet tube.

3. The nebulizer according to claim 1, further comprising:
    at least one support member incorporated onto the reservoir base to establish free-standing capability of the nebulizer on a substantially level surface.

4. The nebulizer according to claim 1, wherein the inlet tube is configured to project into the cistern above the top surface of the substance when received in the storage vessel of the cistern to establish an anti-siphon capability for the nebulizer.

5. The nebulizer according to claim 1, wherein the orifice of the inlet tube is sized to regulate the flow of a pressurized fluid communicated through the inlet tube and to communicate a stream of such fluid into the vacuum space in the direction of the jet nozzle.

6. The nebulizer according to claim 1, wherein the base reservoir includes at least one diffuser standoff adapted to seat the diffuser in the vessel portion of the cistern above a surface of the vessel portion.

7. The nebulizer according to claim 1, wherein the base reservoir includes at least one capture latch adapted to releasably secure the diffuser in the vessel portion of the cistern.

8. The nebulizer according to claim 1, wherein the orifice of the inlet tube is formed to have a cross-sectional area that is approximately less than or equal to the cross-sectional area of the jet nozzle of the diffuser.

9. The nebulizer according to claim 1, wherein the reservoir base is formed to have a generally diminishing lateral cross section from a superior portion to an inferior portion in the storage vessel whereby the substance received in the storage vessel pools about the inferior portion to maximize immersion of a footer disc of the diffuser in the pooled substance.

10. The nebulizer according to claim 1, wherein the diffuser also includes one or more baffle arms.

11. The nebulizer of claim 1, wherein the vent cap, diffuser, and reservoir base are separate components.

12. The nebulizer of claim 1, wherein the diffuser does not touch the vent cap.

13. A nebulizer, comprising:
a reservoir base formed with an inlet tube and adapted to receive a substance to be dispensed, the inlet tube incorporating an orifice about a distal end of the tube;
an effluent vent cap formed with an aerosol outlet and being removably secured to the reservoir base thereby defining an interior cistern with an upper recess and a lower substance storage vessel for containing the substance;
an interchangeable diffuser optimized to nebulize the substance, said diffuser being not directly connected to the vent cap, being releasably held within the cistern, and being formed with an uptake lumen having at one end a jet nozzle, the lumen configured to be removably engaged about the inlet tube to form a capillary interstice and to axially register the jet nozzle proximate to the orifice establishing a vacuum space therebetween;
wherein the diffuser further includes an integral baffle disperser substantially axially aligned superior to the jet nozzle and configured to deflect and nebulize particles of the substance traveling along a path passing through the orifice and the jet nozzle;
wherein, when the diffuser is held within the cistern, the orifice of the inlet tube is stationary relative to the jet nozzle, and
wherein at least one surface of the diffuser and the inlet tube is treated so as to increase adhesion forces between the at least one surface and the substance to be dispensed to amplify the capillary action of the interstice and whereby the adhesion forces are established to be greater than internal cohesion forces of the substance to be dispensed.

14. A nebulizer, comprising:
a reservoir base formed with an inlet tube and adapted to receive a substance to be dispensed, the inlet tube incorporating an orifice about a distal end of the tube;
an effluent vent cap formed with an aerosol outlet and being removably secured to the reservoir base thereby defining an interior cistern with an upper recess and a lower substance storage vessel for containing the substance;
an interchangeable diffuser optimized to nebulize the substance, said diffuser being not directly connected to the vent cap, being releasably held within the cistern, and being formed with an uptake lumen having at one end a jet nozzle, the lumen configured to be removably engaged about the inlet tube to form a capillary interstice and to axially register the jet nozzle proximate to the orifice establishing a vacuum space therebetween;
wherein the diffuser further includes an integral baffle disperser substantially axially aligned superior to the jet nozzle and configured to deflect and nebulize particles of the substance traveling along a path passing through the orifice and the jet nozzle;
wherein, when the diffuser is held within the cistern, the orifice of the inlet tube is stationary relative to the jet nozzle, and
wherein the jet nozzle is formed in a bulkhead of the uptake lumen that incorporates a substantially lateral channel defined by at least two generally confronting sidewalls, the channel being substantially registered about the jet nozzle to minimize the thickness of the bulkhead proximate to the nozzle and whereby the sidewalls are configured to control the divergence of a fluid stream being communicated from the jet nozzle.

15. A nebulizer, comprising:
a reservoir base formed with an inlet tube and adapted to receive a substance to be dispensed, the inlet tube incorporating an orifice about a distal end of the tube;
an effluent vent cap formed with an aerosol outlet and being removably secured to the reservoir base thereby defining an interior cistern with an upper recess and a lower substance storage vessel for containing the substance;
an interchangeable diffuser optimized to nebulize the substance, said diffuser being releasably held within the cistern and being formed with an uptake lumen having at one end a jet nozzle, the lumen configured to be removably engaged about the inlet tube to form a capillary interstice and to axially register the jet nozzle proximate to the orifice establishing a vacuum space therebetween; and
wherein the diffuser further includes an integral baffle disperser substantially axially aligned superior to the jet nozzle and configured to deflect and nebulize particles of the substance traveling along a path passing through the orifice and the jet nozzle,
wherein the jet nozzle is formed in a bulkhead of the uptake lumen that incorporates a substantially lateral channel defined by at least two generally confronting sidewalls, the channel being substantially registered about the jet nozzle to minimize the thickness of the bulkhead proximate to the nozzle and whereby the sidewalls are arranged to define an angle therebetween approximately in the range of between 5 and 47 degrees to thereby optimize the divergence of a fluid stream being communicated from the jet nozzle.

16. A nebulizer for atomizing and dispensing a substance into an effluent aerosolized airstream, comprising:
a reservoir base including an inlet tube formed in a distal end with an orifice and being adapted to receive the substance;
an effluent vent cap formed with an aerosol outlet and configured to be secured to the reservoir base to thereby define an interior cistern for containing the substance;
an interchangeable diffuser optimized to atomize the substance, said diffuser being not directly connected to the vent cap and being releasably held within the cistern, the diffuser formed with an uptake lumen having a jet nozzle at one end, the lumen being adapted to removably receive the inlet tube and forming an interstice therebetween sized to induce adhesion between molecules of the substance and the confronting walls of the diffuser and inlet tube, the lumen also being adapted to axially register the jet nozzle proximate to the orifice when received on the inlet tube to establish a vacuum space between the nozzle and the orifice;
wherein the diffuser further includes an integral baffle disperser substantially axially aligned superior to the jet nozzle and sized to obstruct, atomize, and deflect particles moving in a line of motion passing through both the orifice and the jet nozzle;

wherein, when the diffuser is held within the cistern, the orifice of the inlet tube is stationary relative to the jet nozzle, and wherein the aerosol outlet of the effluent vent cap is further formed with a baffle lumen projecting interiorly into the upper recess.

17. The nebulizer according to claim 16, further comprising:

at least one support member incorporated onto the reservoir base to establish free-standing capability of the nebulizer on a substantially level surface.

18. The nebulizer according to claim 16, wherein the inlet tube is configured to project into the cistern above the top surface of the substance when received in the storage vessel of the cistern to establish an anti-siphon capability for the nebulizer.

19. The nebulizer according to claim 16, wherein the orifice of the inlet tube is sized to regulate the flow of a pressurized fluid communicated through the inlet tube and to communicate a stream of such fluid into the vacuum space in the direction of the jet nozzle.

20. The nebulizer according to claim 16, wherein the base reservoir includes at least one diffuser standoff adapted to seat the diffuser in the vessel portion of the cistern above a surface of the vessel portion.

21. The nebulizer according to claim 16, wherein the base reservoir includes at least one capture latch adapted to releasably secure the diffuser in the vessel portion of the cistern.

22. The nebulizer according to claim 16, wherein the orifice of the inlet tube is formed to have a cross-sectional area that is approximately less than or equal to the cross-sectional area of the jet nozzle of the diffuser.

23. The nebulizer according to claim 16, wherein the reservoir base is formed to have a generally diminishing lateral cross section from a superior portion to an inferior portion in the storage vessel whereby the substance received in the storage vessel pools about the inferior portion to maximize immersion of a footer disc of the diffuser in the pooled substance.

24. The nebulizer of claim 16, wherein the vent cap, diffuser, and reservoir base are separate components.

25. The nebulizer of claim 16, wherein the diffuser does not touch the vent cap.

26. A nebulizer for atomizing and dispensing a substance into an effluent aerosolized airstream, comprising:

a reservoir base including an inlet tube formed in a distal end with an orifice and being adapted to receive the substance;

an effluent vent cap formed with an aerosol outlet and configured to be secured to the reservoir base to thereby define an interior cistern for containing the substance;

an interchangeable diffuser optimized to atomize the substance, said diffuser being not directly connected to the vent cap and being releasably held within the cistern, the diffuser formed with an uptake lumen having a jet nozzle at one end, the lumen being adapted to removably receive the inlet tube and forming an interstice therebetween sized to induce adhesion between molecules of the substance and the confronting walls of the diffuser and inlet tube, the lumen also being adapted to axially register the et nozzle proximate to the orifice when received on the inlet tube to establish a vacuum space between the nozzle and the orifice;

wherein the diffuser further includes an integral baffle disperser substantially axially aligned superior to the jet nozzle and sized to obstruct, atomize, and deflect particles moving in a line of motion passing through both the orifice and the jet nozzle;

wherein, when the diffuser is held within the cistern, the orifice of the inlet tube is stationary relative to the jet nozzle, and wherein at least one surface of the diffuser and the inlet tube is treated so as to increase adhesion forces between the at least one surface and the substance to be dispensed to amplify a capillary action of the interstice and whereby the adhesion forces are established to be greater than internal cohesion forces of the substance to be dispensed.

27. A nebulizer for atomizing and dispensing a substance into an effluent aerosolized airstream, comprising:

a reservoir base including an inlet tube formed in a distal end with an orifice and being adapted to receive the substance;

an effluent vent cap formed with an aerosol outlet and configured to be secured to the reservoir base to thereby define an interior cistern for containing the substance;

an interchangeable diffuser optimized to atomize the substance, said diffuser being not directly connected to the vent cap and being releasably held within the cistern, the diffuser formed with an uptake lumen having a jet nozzle at one end, the lumen being adapted to removably receive the inlet tube and forming an interstice therebetween sized to induce adhesion between molecules of the substance and the confronting walls of the diffuser and inlet tube, the lumen also being adapted to axially register the let nozzle proximate to the orifice when received on the inlet tube to establish a vacuum space between the nozzle and the orifice;

wherein the diffuser further includes an integral baffle disperser substantially axially aligned superior to the jet nozzle and sized to obstruct, atomize, and deflect particles moving in a line of motion passing through both the orifice and the jet nozzle;

wherein, when the diffuser is held within the cistern, the orifice of the inlet tube is stationary relative to the jet nozzle, and wherein the jet nozzle is formed in a bulkhead of the uptake lumen that incorporates a substantially lateral channel defined by at least two generally confronting sidewalls, the channel being substantially registered about the jet nozzle to minimize the thickness of the bulkhead proximate to the nozzle and whereby the sidewalls are configured to control the divergence of a fluid stream being communicated from the jet nozzle.

28. A nebulizer for atomizing and dispensing a substance into an effluent aerosolized airstream, comprising:

a reservoir base including an inlet tube formed in a distal end with an orifice and being adapted to receive the substance;

an effluent vent cap formed with an aerosol outlet and configured to be secured to the reservoir base to thereby define an interior cistern for containing the substance;

an interchangeable diffuser optimized to atomize the substance, said diffuser being releasably held within the cistern, the diffuser formed with an uptake lumen having a jet nozzle at one end, the lumen being adapted to removably receive the inlet tube and forming an interstice therebetween sized to induce adhesion between molecules of the substance and the confronting walls of the diffuser and inlet tube, the lumen also being adapted to axially register the jet nozzle proximate to the orifice when received on the inlet tube to establish a vacuum space between the nozzle and the orifice; and wherein the diffuser further includes an integral baffle disperser substantially axially aligned superior to the jet nozzle and sized to obstruct, atomize, and deflect particles moving in a line of motion passing through both the orifice and the jet nozzle, wherein the jet nozzle is formed in a bulkhead of the uptake lumen that incorporates a substantially lateral channel defined by at least two generally confronting sidewalls, the channel being substantially registered about the jet nozzle to minimize the thickness of the bulkhead proximate to the nozzle and whereby the sidewalls are arranged to define an angle therebetween approximately in the range of between 5 and 47 degrees to thereby optimize the divergence of a fluid stream being communicated from the jet nozzle.

29. A nebulizer for dispensing a substance to be inhaled by a patient, comprising:

an effluent vent cap formed with an aerosol outlet;

a reservoir base configured to be removably secured to the effluent cap to define a cistern, the reservoir base being adapted to receive the substance and incorporating an inlet tube formed with an internal lumen terminating at a distal orifice;

a diffuser optimized for use with the substance and adapted to be secured within the cistern and formed with an uptake channel adapted to receive the inlet tube to substantially form a capillary interstice configured to maximize uptake of the substance through the interstice, the uptake channel terminating at one end with a jet nozzle sized to be approximately larger than or equal to the distal orifice and that, upon receipt of the inlet tube within the channel, is axially registered proximate with the orifice to establish a vacuum space between the nozzle and the orifice;

wherein the diffuser further includes an integral baffle disperser substantially axially aligned superior to the jet nozzle and sized to obstruct, break apart, and accelerate atomized particles of the substance moving in a line of motion passing through both the orifice and the jet nozzle; and a substantially lateral groove formed in the terminating end of the uptake channel and defined by at least two generally confronting sidewalls and a substantially flat bottom, the groove being substantially registered about the jet nozzle to minimize the thickness of the terminating end proximate the nozzle and whereby the sidewalls define an angle therebetween selected to optimize the divergence of a fluid stream being communicated from the jet nozzle.

30. The nebulizer according to claim 29, wherein the aerosol outlet of the effluent vent cap is further formed with a baffle lumen projecting interiorly into the upper recess.

31. The nebulizer according to claim 29, further comprising:

at least one support member incorporated onto the reservoir base to establish free-standing capability of the nebulizer on a substantially level surface.

32. The nebulizer according to claim 29, wherein the inlet tube is configured to project into the cistern above the top surface of the substance when received in the storage vessel of the cistern to establish an anti-siphon capability for the nebulizer.

33. The nebulizer according to claim 29, wherein the orifice of the inlet tube is sized to regulate the flow of a pressurized fluid communicated through the inlet tube and to communicate a stream of such fluid into the vacuum space in the direction of the jet nozzle.

34. The nebulizer according to claim 29, wherein the base reservoir includes at least one diffuser standoff adapted to seat the diffuser in an inferior portion of the cistern above a bottom surface of the cistern.

35. The nebulizer according to claim 29, wherein the base reservoir includes at least one capture latch adapted to releasably secure the diffuser in the vessel portion of the cistern.

36. The nebulizer according to claim 29, wherein the reservoir base is formed to have a generally diminishing lateral cross section from a superior portion to an inferior portion in the storage vessel whereby the substance received in the storage vessel pools about the inferior portion to maximize immersion of a footer disc of the diffuser in the pooled substance.

37. The nebulizer according to claim 29, wherein at least one surface of the uptake channel and the inlet tube is treated so as to optimize the capillary action of the interstice for the substance.

38. The nebulizer according to claim 29, wherein the diffuser also includes one or more baffle arms.

39. The nebulizer of claim 29, wherein the confronting sidewalls do not intersect.

40. A nebulizer for dispensing a substance to be inhaled by a patient, comprising:

an effluent vent cap formed with an aerosol outlet;

a reservoir base configured to be removably secured to the effluent cap to define a cistern, the reservoir base being adapted to receive the substance and incorporating an inlet tube formed with an internal lumen terminating at a distal orifice;

a diffuser optimized for use with the substance and adapted to be secured within the cistern and formed with an uptake channel adapted to receive the inlet tube to substantially form a capillary interstice configured to maximize uptake of the substance through the interstice, the uptake channel terminating at one end with a jet nozzle sized to be approximately larger than or equal to the distal orifice and that, upon receipt of the inlet tube within the channel, is axially registered proximate with the orifice to establish a vacuum space between the nozzle and the orifice;

wherein the diffuser further includes an integral baffle disperser substantially axially aligned superior to the jet nozzle and sized to obstruct, break apart, and accelerate atomized particles of the substance moving in a line of motion passing through both the orifice and the jet nozzle; and a substantially lateral groove formed in the terminating end of the uptake channel and defined by at least two generally confronting sidewalls, the groove being substantially registered about the jet nozzle to minimize the thickness of the terminating end proximate the nozzle and whereby the sidewalls define an angle therebetween selected to optimize the divergence of a fluid stream being communicated from the jet nozzle, wherein the angle defined by the confronting sidewalls is approximately in the range of between 5 and 47 degrees.

41. A system for nebulization and dispensing at least two treatment substances, comprising:

a reservoir base adapted to receive a quantity of at least one of the substances, the reservoir base including a pressurized fluid inlet tube terminating in a distal metering orifice;

an effluent vent cap formed with an aerosol outlet and being coupled to the reservoir base to define an interior cistern with an upper recess and a lower substance storage vessel adapted to contain at least one of the substances;

a plurality of interchangeable diffusers each optimized for a different set of nebulization parameters and to be releasably secured to the reservoir base and being formed with an uptake lumen in fluid communication with the storage vessel and terminating at one end with a nozzle jet formed with a divergent spray guide, the lumen configured to be removably engaged about the inlet tube to substantially form a capillary interstice therewith and to axially register the nozzle jet proximate to the orifice to establish, during operation, a vacuum space between the nozzle jet and the orifice; and wherein at least one diffuser of the plurality further includes an integral dispersing baffle substantially axially aligned superior to the jet nozzle and configured to obstruct, atomize, and accelerate particles of the at least one of the substances traveling along a path passing through both the orifice and the jet nozzle.

42. The nebulizer of claim 41, wherein the plurality of interchangeable diffusers have varying configurations.

43. A nebulizer, comprising:

a reservoir base formed with an inlet tube and adapted to receive a substance to be dispensed, the inlet tube incorporating an orifice about a distal end of the tube;

an effluent vent cap formed with an aerosol outlet and being removably secured to the reservoir base thereby defining an interior cistern with an upper recess and a lower substance storage vessel for containing the substance;

an interchangeable diffuser optimized to nebulize the substance, said diffuser being not directly connected to the vent cap, being releasably held within the cistern, and being formed with an uptake lumen having at one end a jet nozzle, the lumen configured to be removably engaged about the inlet tube to form a capillary interstice and to axially register the jet nozzle proximate to the orifice establishing a vacuum space therebetween;

wherein the diffuser further includes an integral baffle disperser substantially axially aligned superior to the jet nozzle and configured to deflect and nebulize particles of the substance traveling along a path passing through the orifice and the jet nozzle; and wherein at least one surface of the diffuser and the inlet tube is treated so as to increase adhesion forces between the at least one surface and the substance to be dispensed.

44. The nebulizer of claim 43, wherein the at least one surface is treated to amplify the capillary action of the interstice, and whereby the adhesion forces are established to be greater than internal cohesion forces of the substance to be dispensed.

45. A nebulizer for atomizing and dispensing a substance into an effluent aerosolized airstream, comprising:

a reservoir base including an inlet tube formed in a distal end with an orifice and being adapted to receive the substance;

an effluent vent cap formed with an aerosol outlet and configured to be secured to the reservoir base to thereby define an interior cistern for containing the substance;

an interchangeable diffuser optimized to atomize the substance, said diffuser being not directly connected to the vent cap and being releasably held within the cistern, the diffuser formed with an uptake lumen having a jet nozzle at one end, the lumen being adapted to removably receive the inlet tube and forming an interstice therebetween sized to induce adhesion between molecules of the substance and the confronting walls of the diffuser and inlet tube, the lumen also being adapted to axially register the jet nozzle proximate to the orifice when received on the inlet tube to establish a vacuum space between the nozzle and the orifice;

wherein the diffuser further includes an integral baffle disperser substantially axially aligned superior to the jet nozzle and sized to obstruct, atomize, and deflect particles moving in a line of motion passing through both the orifice and the jet nozzle; and wherein at least one surface of the diffuser and the inlet tube is treated so as to increase adhesion forces between the at least one surface and the substance to be dispensed.

46. The nebulizer according to claim 45, wherein the at least one surface is treated to amplify a capillary action of the interstice, and whereby the adhesion forces are established to be greater than internal cohesion forces of the substance to be dispensed.

* * * * *